US011315668B2

(12) United States Patent
Castine et al.

(10) Patent No.: US 11,315,668 B2
(45) Date of Patent: Apr. 26, 2022

(54) ABSTRACTING INFORMATION FROM PATIENT MEDICAL RECORDS

(71) Applicant: ASTRATA, INC., Pittsburgh, PA (US)

(72) Inventors: Melissa Castine, Pittsburgh, PA (US); Girish Chavan, Pittsburgh, PA (US); Carly Cook, Pittsburgh, PA (US); Rebecca Jacobson, Pittsburgh, PA (US); Jody Madala, Pittsburgh, PA (US); Amy Malanga, Pittsburgh, PA (US); Eugene Tseytlin, Pittsburgh, PA (US); Adam Yee, Pittsburgh, PA (US)

(73) Assignee: Astrata, Inc., Pittsburgh, PA (US)

( * ) Notice: Subject to any disclaimer, the term of this patent is extended or adjusted under 35 U.S.C. 154(b) by 0 days.

(21) Appl. No.: 17/060,518

(22) Filed: Oct. 1, 2020

(65) Prior Publication Data

US 2021/0020281 A1 Jan. 21, 2021

Related U.S. Application Data

(62) Division of application No. 16/178,395, filed on Nov. 1, 2018.

(51) Int. Cl.
*G16H 10/60* (2018.01)
*G16H 50/30* (2018.01)
*G06F 16/35* (2019.01)

(52) U.S. Cl.
CPC ............ *G16H 10/60* (2018.01); *G06F 16/35* (2019.01); *G16H 50/30* (2018.01)

(58) Field of Classification Search
CPC ......... G16H 10/60; G16H 50/30; G06F 16/35
See application file for complete search history.

(56) References Cited

U.S. PATENT DOCUMENTS

| 2002/0082863 | A1  | 6/2002  | Kleinke |
| 2005/0234740 | A1  | 10/2005 | Krishnan et al. |
| 2012/0066031 | A1* | 3/2012  | Chao ................. G06Q 10/00 705/7.39 |
| 2013/0185089 | A1  | 7/2013  | Michelson et al. |

(Continued)

OTHER PUBLICATIONS

Breslau et al. Biological Psychiatry vol. 39, Issue 6, Mar. 15, 1996, pp. 411-418, "Sleep disturbance and psychiatric disorders: A longitudinal epidemiological study of young Adults" (Year: 1996).*

(Continued)

*Primary Examiner* — John P Go
*Assistant Examiner* — Chad A Newton
(74) *Attorney, Agent, or Firm* — Fish & Richardson P.C.

(57) ABSTRACT

Among other things, unstructured text items are processed to identify elements of the unstructured text items relevant to classification rules of quality metrics applicable to services provided by a healthcare provider with respect to diseases, conditions, or interventions of patients. The classification rules define classifications of patients based on diseases, conditions, or interventions of patients or on aspects of the services provided. Through a user interface, the unstructured text items, the identified elements, and user interface controls for classifying the patients with respect to the classification rules, based on the identified elements, are presented to the user.

20 Claims, 12 Drawing Sheets

(56) References Cited

U.S. PATENT DOCUMENTS

Figure 1:
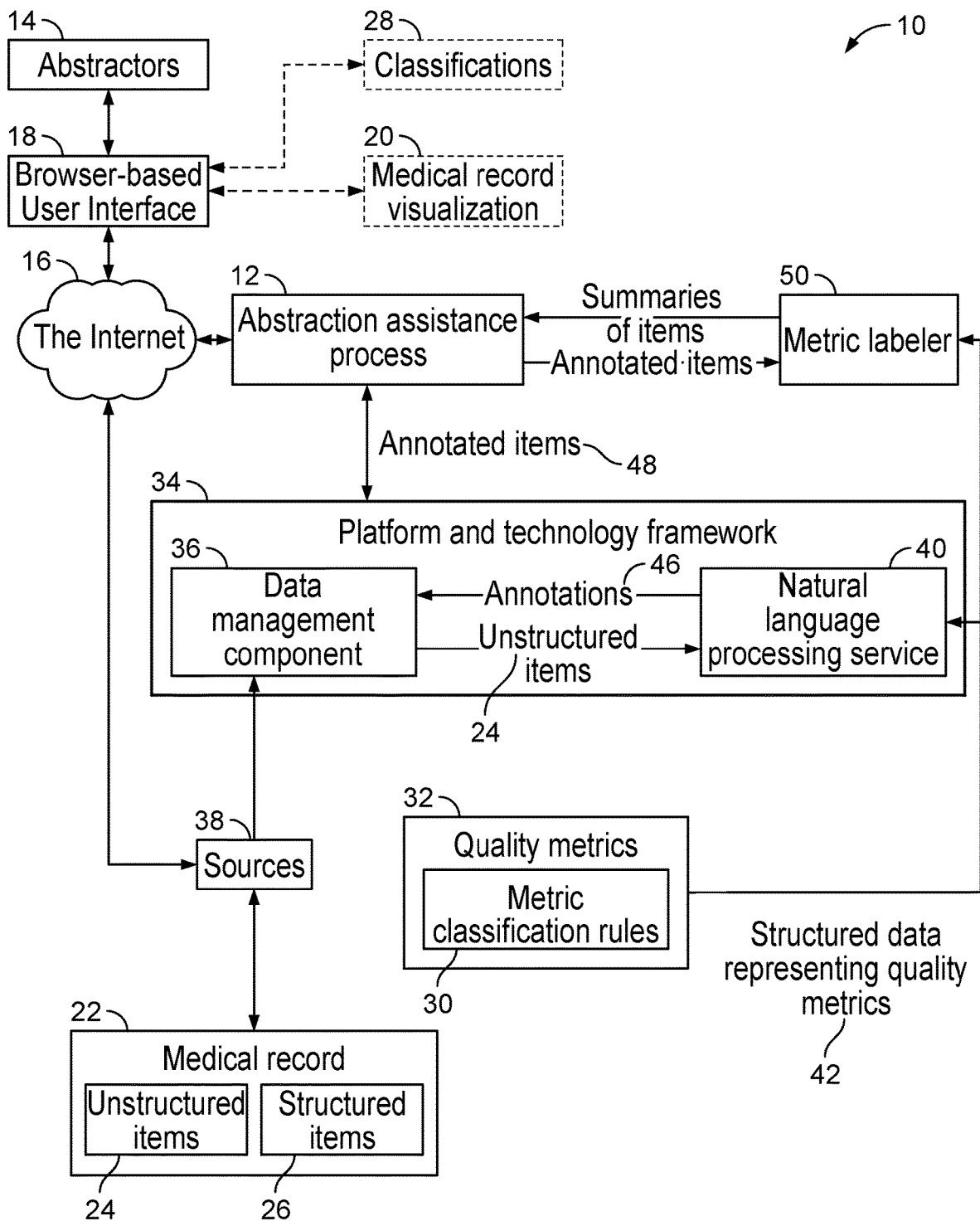

| | | | | |
|---|---|---|---|---|
| 2014/0365210 | A1* | 12/2014 | Riskin | G16H 15/00 |
| | | | | 704/9 |
| 2015/0066539 | A1* | 3/2015 | Sheffer | G16H 50/20 |
| | | | | 705/3 |
| 2015/0081324 | A1* | 3/2015 | Adjaoute | G06Q 40/08 |
| | | | | 705/2 |
| 2015/0213225 | A1 | 7/2015 | Amarasingham et al. | |
| 2017/0132371 | A1* | 5/2017 | Amarasingham | G06F 40/30 |

OTHER PUBLICATIONS

Hirsch, Jamie S. et al., "Harvest, a longitudinal patient records summarizer", J Am Med Inform Assoc 2015;22:263-274. doi:10.1136/amiajnl-2014-002945, Research and Applications, 23 pages, Oct. 28, 2014.

Noble Tools, "Noble Coder: Named Entity Recognition (NER) engine for biomedical text", http://nobletools.dbmi.pitt.edu, retrieved from the Internet on Apr. 9, 2019 (6 pages).

Denny et al., "Natural language processing improves identification of colorectal cancer testing in the electronic medical record," Medical Decision Making 32(1): 188-197, Jan. 2012.

Garvin et al., "Automated quality measurement in department of the veterans affairs discharge instructions for patients with congestive heart failure," Journal of Healthcare Quality 35(4):16-24, Jul. 2013.

Garvin et al., "Automating quality measures for heart failure using natural language processing: a descriptive study in the department of veterans affairs," JMIR medical informatics 20(1):1-14, 2018.

Harkema et al., "Developing a natural language processing application for measuring the quality of colonoscopy procedures," Journal of the American Medical Informatics Association 18(Suppl):i150-i156, Sep. 2011.

Imler et al., "Multi-center colonoscopy quality measurement utilizing natural language processing," American Journal of Gastroenterology 110(4):543-552, Apr. 2015.

Imler et al., "Provider-specific quality measurement for ERCP using natural language processing," Gastrointestinal Endoscopy 87(1):164-173, Jan. 2018.

Kerr et al., "Measuring physician adherence with gout quality indicators: A role for natural language processing," Arthritis Care and Research 67(2):273-279, Feb. 2015.

Mehrotra et al., "Applying a natural language processing tool to electronic health records to assess performance on colonoscopy quality measures," Gastrointestinal Endoscopy 75(6):1233-1239, Jun. 2012.

Meystre et al., "Congestive heart failure information extraction framework for automated treatment performance measures assessment," Journal of the American Medical Informatics Association 24(e1):e40-e46, Jul. 2016.

Nayor et al., "Natural Language Processing Accurately Calculates Adenoma and Sessile Serrated Polyp Detection Rates," Digestive Diseases and Sciences, pp. 1794-1800, Jul. 2018.

International Search Report & Written Opinion in International Application No. PCT/US2019/054457 dated Feb. 27, 2020, 8 pages.

Breslau et al., "Sleep disturbance and psychiatric disorders: A longitudinal epidemiological study of young Adults," Biological Psychiatry: vol. 39, Issue 6, Mar. 15, 1996: pp. 411-418.

* cited by examiner

FIG. 3

Patient: Penelope MIDDLE Pussycat | MRN: 507
Age: 59 | DOB: 05/27/1959 | Gender: Female

| | | 507 | | OP-30 | | 9 | | Find Patient |

Documents Summary
Filter relevant documents by metric inclusion and/or exclusion criteria

| | *MRN Required | *MRN Required | *FIN Required |

| Numerator Inclusion ⌄ | Numerator Exclusion ⌄ | Denominator Inclusion ⌄ | Denominator Exception ⌄ |
| No evidence found | No evidence found — 169 | Prev colonoscopy | Diverticulosis Hemorrhoids |

⊟ Relevant Docu... (6)   Sort by [Relevance ▶]

⊟ Additional Doc... (76)

Document Type   DEFAULT_DocumentType...
Creation Date    Jan 24, 2014 | 10:44:00 PM
Source System   Cerner
FIN Number        7
[Prev colonoscopy]  Diverticulosis
Hemorrhoids
                     └─ 171

Document Type   DEFAULT_DocumentType...
Creation Date    Jan 24, 2014 | 5:48:00 PM
Source System   Cerner
FIN Number        7
Diverticulosis Hemorrhoids Document Type   DEFAULT_DocumentType...
Creation Date    Jul 27, 2016 | 2:26:00 PM
Source System   Cerner
FIN Number        8
Diverticulosis Document Type   DEFAULT_DocumentType...
Creation Date    Jul 27, 2016 | 2:24:00 PM
Source System   Cerner
FIN Number        8

Document Type
DEFAULT_DocumentTypeOfServiceExtension -
DEFAULT_DocumentKindOfDocumentExtension
Physician Name FIRST LAST
Creation Date Jan 24, 2014 | 10:44:00 PM
Source System Cerner
FIN Number 7

☐ Denominator Inclusion  — 168
[Prev colonoscopy]
☐ Denominator Exception
Diverticulosis Hemorrhoids ⊕⊖
[ Navigate Selection(s)   ↑  ↓ ]

s. As you know, the patient had a prior history of a [colonoscopy] It was either unlikely an anal-arkable, I would reco-consistent with a condyloma versus -mmend a repeat EGO in 3 years' time.
We wil-

— 170

▦  Was this document helpful? | View Original

⇤ Logout

FIG. 4

FIG. 5

Patient: Penelope MIDDLE Pussycat | MRN: 507
Age: 59 | DOB: 05/27/1959 | Gender: Female

| ⊙ Numerator Inclusion ▶ | ☑ Denominator Inclusion ▶ | OP30 ▶ | Jun 22, 2007 - Jun 22, 2017 | 3 Years ▶ | 🔍 Find Patient... |
|---|---|---|---|---|
| Colonoscopy<br>Previous Colonoscopy | Colonic Polyp<br>Polypectomy | ⊙ Numerator Exclusion ▶<br>No matches found | ☐ Denominator Exclusion ▶<br>Family History Colorectal Cancer<br>Difficult Scope<br>Diverticulosis Diagnosis | |

174

Matching Documents (6)

| | Matching Documents (6) | ▲ Date ▼ |
|---|---|---|
| | Document Type  Colonoscopy Report<br>Creation Date  June 22, 2017<br>Physican Name  Dr. Don Dee | |
| | Previous Colonoscopy Colonoscopy Colonic Polyp<br>Polypectomy   Family History Colorectal Cancer<br>Diverticulosis | 1 |
| | Document Type  Inoperative Report<br>Creation Date  June 22, 2017<br>Physican Name  Dr. Don Dee | |
| | Colonoscopy   Diverticulosis | |
| | Document Type  Progress Note<br>Creation Date  January 22, 2015<br>Physican Name  Dr. Don Dee | |
| | Previous Colonoscopy Colonic Polyp Polypectomy | |
| | Document Type  Colonoscopy<br>Creation Date  January 31, 2013<br>Physican Name  Dr. Don Dee | |
| | Previous Colonoscopy Difficult Scope | |

Other Clinical Notes (21)

Document type Colonoscopy
Physician Name Dr. Don Dee
Creation Date January 22, 2015
Source System Cerner ☐ Numerator Inclusion
Previous Colonoscopy
Colonoscopy ☐ Denominator Inclusion
Colonic Polyp Polypectomy UPMC Magee Women's Hospital
Division of Gastroenterology
Patient Name: Penelope Pussycat
MRN: 1789654736
Date of Birth: 04/16/1949
Admit Type: Outpatient
Procedure Date: 01/22/2015 9:09 AM
Age: 59
Gender: Female
Patient Location: GSDS
Procedure: Colonoscopy
Indications: Screening for colorectal malignant ne
            Follow-up for history of adenomatous
            polyps in the colon Last colonoscopy
Providers:   Don Dee, MD(Doctor)
Medicines: Monitored Anesthesia Care
Complications: No immediate complications.
Procedure: After I obtained informed consent, the
            was passed under direct vision. Throu
            procedure, the patient's blood pressur
            oxygen saturations were monitored co You may also be interested in:

📄                    📄
Colonoscopy      Colonoscopy
06/22/17         01/31/2013

📄 Was this document helpful?     View Original

ABSTRACTING INFORMATION FROM PATIENT MEDICAL RECORDS

RELATED APPLICATIONS

This application is a divisional of U.S. patent application Ser. No. 16/178,395, filed on Nov. 1, 2018, the entire contents of which are incorporated here by reference.

BACKGROUND

This description relates to abstracting information from patient medical records.

A patient medical record (also sometimes called a patient chart) is typically an aggregation of information (sometimes from multiple sources) documenting a patient's medical history and care over time as provided by one or more health care providers, such as a clinical practice or a hospital. The documents and other items in a patient medical record can include unstructured natural language items, for example, prose notes of physicians, and structured items, for instance, numerical data about services and pharmaceuticals provided to the patient, images, and the results of tests, among other things.

The documents and other items in patient medical records reveal the quality of services delivered by the health care provider to individual patients and to groups of patients with respect to particular diseases, conditions, or procedures. The quality of the services can include the provider's adherence to accepted protocols and the success of outcomes, among others.

Review and analysis of patient medical records is required to determine the quality of service by providers for given diseases, conditions, or procedures for individual patients and groups of patients. For example, a patient medical record can indicate that no follow-up colonoscopy was performed on a particular patient within a number of years (specified in standard protocols) after an adenoma had been identified in a prior colonoscopy. To derive such a conclusion from the medical record can require time consuming human study of prose notes and other parts of the medical record to understand which procedures were performed, when, and with what outcomes.

Information about the quality of service derived from medical records can be useful to the health care provider in evaluating its historical performance and altering its procedures to improve future performance. Such information can also be useful to insurers, other payers, regulators, and other parties.

Third parties sometimes define and promulgate detailed quality metrics for evaluating performance of health care providers with respect to particular diseases, conditions, or interventions. The third parties may require the health care providers to report the quality metrics, which are sometimes seen as indicators of the value of the services provided. Payments to the providers can be conditioned on receipt of the reports and on whether the reported quality metrics meet defined performance standards. For example, quality metrics support so-called pay-for-reporting programs such as the CMS Hospital OQR Program for hospital outpatient services mandated by the Tax Relief and Health Care Act of 2006. The quality metrics also support pay-for-performance programs such as the Healthcare Effectiveness Data and Information Set (HEDIS) used to determine CMS payments to healthcare payers.

Some quality metrics are expressed as simple fractions. The denominator of the fraction may be the total number of patients having a certain disease or condition or intervention and who were served by the provider in a given period. The numerator may be the number of those patients for whom a particular protocol was followed or a particular outcome was achieved.

An example of a quality metric is Measure #343 titled "Screening Colonoscopy Adenoma Detection Rate [ADR]," defined by the American Medical Association (AMA). The denominator of that measure is all of the provider's patients 50 years or older undergoing a screening colonoscopy. The numerator is the number of such patients with at least one conventional adenoma or colorectal cancer detected during screening colonoscopy.

To enable uniform and consistent measurement and reporting, quality metrics expressed as fractions have classification rules defining how patients are to be categorized within the denominator and the numerator. In most cases, the quality metrics also define classification rules for exclusion of patients from the denominator or the numerator.

Using the classification rules to determine which patients fall within the denominator and which of those patients fall within the numerator often requires careful time-consuming study by a human being of unstructured natural language items in the medical record. The documents and other items of the medical record are typically stored electronically and can be reviewed through a user interface of a computer or other device, for example, remotely using a Web browser. The work, sometimes called chart abstraction, is largely manual and is tedious.

In a typical workflow sequence for manual chart abstraction, abstractors directly inspect the medical record stored in an online electronic medical record system and express the insights of their abstraction work using abstraction workflow management tools (computer applications) such as the Cerner EQC tool (and Centauri Health Solution's Centauri Ascent tool). These abstraction workflow management tools are often integrated with the electronic medical record system so that the denominator can be automatically defined based on billing codes. In some examples, after launching the electronic medical record system, the user manually enters a physician's name and searches for a patient's medical record using the patient's medical record number (MRN). Once the medical record is presented in the user interface, the user can filter by date to review relevant items of the medical record. The EQC or other abstraction workflow management tool generates a work queue for each quality metric which can be applied by the abstractor with respect to the patient's medical record. In the work queue for each metric, the abstraction workflow management tool displays a form with questions that may either be automatically populated by the abstraction workflow management tool using stored structured data or be answered by the abstractor by reading through relevant unstructured natural language items of the medical record.

Providers typically allocate many employee hours to have chart abstractors generate accurate classifications of patients based on medical records.

Fractions such as ADR are only one kind of quality metric. Other kinds of quality metrics for providers or payers may be defined by other types of rules that recite how patients are to be evaluated for purposes of the quality metrics, based on their medical records.

SUMMARY

In general, in an aspect, unstructured text items are processed automatically to identify elements of the unstructured text items relevant to classification rules of quality metrics applicable to services provided by a healthcare provider with respect to diseases, conditions, or interventions by healthcare providers. The classification rules define classifications of patients based on diseases, conditions, or procedures of patients or on aspects of the services provided. Through a user interface, the unstructured text items, the identified elements, and user interface controls for review and classifications of, or classifying the patients with respect to the classification rules, based on the identified elements, are presented to the user.

Implementations may include one or a combination of two or more of the following features. The processing includes processing of structured data items to identify elements of the structured data items relevant to the classification rules. The processing of the unstructured text items includes natural language processing. The processing of the unstructured text items includes specifying metadata (e.g., annotations) for the unstructured text items, the metadata including factors of the classification rules applicable to the unstructured text items. The metadata is specified at a mention level (e.g., specific pieces of text in the unstructured text item) and at the item level (e.g., metadata that applies to the item overall). The metadata for unstructured text items is of one or more types (e.g., a type associated with a classification rule to which it pertains). Structured data is maintained representing the classification rules and the specifying of metadata for the unstructured text items is based on the structured data representing the classification rules. The identified elements of the unstructured text items include at least one of words, phrases, concepts, modifiers (e.g., negation, experiencer, or temporal quality associated with the concept), or relationships (e.g., drugs that treat diseases or temporal relationships between events). A user interface control for specifying a range of dates is presented through the user interface, and the unstructured text items presented to each of the users are within the range of dates. The unstructured text items include notes of one or more practitioners. The quality metrics include fractions. The classification rules define denominators of the fractions as patients in populations having specified characteristics. The classification rules define numerators of the fractions as numbers of patients who belong to the populations of the denominators and for whom diseases, conditions, or interventions of the patients, or services provided the healthcare provider have specified factors. The denominators of the fractions include numbers of patients satisfying first classification rules of the quality metric, and the numerators of the fractions includes numbers of patients satisfying second classification rules of the quality metric. The presenting by the computer, through the user interface, of the unstructured text items includes identifying for the users, unstructured text items based on their relevance status to the classification rules. The presenting by the computer, through the user interface, of the unstructured text items includes presenting the unstructured text items in orders based on their dates or relevances. The presenting by the computer, through a user interface, of the unstructured text items includes presenting a summary of classification statuses of the patients with respect to the classification rules.

In general, in an aspect, files are received of unstructured text and annotations identifying elements of the unstructured text relevant to classification rules of quality metrics applicable to services provided by a healthcare provider with respect to diseases, conditions, or interventions of patients. Structured data is received representing the classification rules. By computer, the unstructured text and annotations are processed using the structured data representing the classification rules to generate indications of conformity of the unstructured text with the classification rules.

Implementations may include one or a combination of two or more of the following features. The processing of the unstructured text and annotations includes parsing the unstructured text and annotations to identify elements of annotations matching elements of the structured data representing the classification rules. The unstructured text includes human-generated prose. The annotations include words, phrases, modifiers, or concepts. The quality metrics include fractions and the classification rules define criteria for inclusion in the numerators or the denominators of the fractions. By computer, pages of the user interface are populated with the unstructured text, the identified elements of the unstructured text, and the indications of conformity of the unstructured text with the classification rules.

In general, in an aspect, a computer system is configured to run one or more processes to populate and serve pages of a user interface through a communication network to a web browser or an application. The user interface is configured for reviewing items of a patient medical record and reviewing or generating indications of conformity of the patient medical record with rules of quality metrics. The quality metrics are applicable to services provided by healthcare providers with respect to diseases, conditions, or interventions of patients. Included in the populated and served pages are (a) unstructured text and annotations identifying elements of the unstructured text relevant to the rules of the quality metrics, (b) the indications of conformity, (c) user interface controls for indicating conformity of the patient medical record with the rules of the quality metrics, (d) structured metadata elements associated with the unstructured text, and € structured data elements in the patient medical record. There is a coordination of processing of (d) unstructured text items of the patient medical record to generate annotations, and (e) annotations of the unstructured text items to generate the indications of conformity.

In general, in an aspect, a user interface includes a presentation of an unstructured text and annotations identifying elements of the unstructured text relevant to classification rules of quality metrics applicable to services provided by healthcare with respect to diseases, conditions, or interventions of patients. The user interface includes a presentation of indications of conformity of the unstructured text with the classification rules. And the user interface includes a presentation of user interface controls for navigating additional unstructured texts and annotations and for indicating conformity of each of the unstructured text annotations with the classification rules.

In general, in an aspect, electronic medical records are maintained for a population of patients of a healthcare provider. The electronic medical records including information about diseases, conditions, or interventions of the patients. Each of the patients is classified according to classification rules of quality metrics applicable to services provided by the healthcare provider with respect to the diseases, conditions, or procedures. The classifying includes automated classification by computer. Results of the automated classification are presented through a user interface. The classification is altered based on inputs through the user interface received from a human being.

In general, in an aspect, an electronic medical record system includes storage for electronic medical records of a population of patients of a healthcare provider. The electronic medical records include information about diseases, conditions, or interventions of the patients. A user interface of the electronic medical record system is presented by computer. The user interface includes user interface controls for interacting with the electronic medical record system. A quality metric process is configured to use information in the electronic medical records to classify patients according to classification rules of quality metrics. A user interface includes user interface controls for interacting with the electronic medical record system and the quality metric process in the same user interface.

In general, in an aspect, a quality metric measurement process is run by computer. A user interface is presented including user interface controls for the quality metric measurement process. The quality metric measurement process is configured to automatically classify patients of a healthcare provider according to classification rules of quality metrics. The user interface controls are configured for classification of patients by human users. A performance of the quality metric measurement process in automatically classifying patients is compared against a performance of the human users in classifying the same patients.

In general, in an aspect, a quality metric measurement process is run by computer. A first user interface is presented including user interface controls for classification by users of patients of a healthcare provider according to classification rules of quality metrics. The classification rules include structured data representing natural language classification rules. A second user interface is presented including user interface controls for management of the quality metric measurement process. The user interface controls of the second user interface include user interface controls for updating the structured data representing the natural language classification rules. The presentation of the first user interface is updated in response to the updating of the structured data representing the natural language classification rules.

In general, in an aspect, a healthcare provider provides service to a patient with respect to a disease, condition, or procedure. Classification rules of a quality metric are automatically applied to a stored electronic medical record of the patient to determine compliance of the healthcare provider with a protocol corresponding to the quality metric. Through a user interface of a medical record system containing the stored electronic medical record of the patient, the determined compliance is reported to the healthcare provider, and the healthcare provider adjusts the service to the patient based on the reported compliance.

In general, in an aspect, elements of an unstructured text item of an electronic medical record of the patient are identified that are relevant to a classification rule of a quality metric applicable to a healthcare provider with respect to a disease, condition, or procedure of the patient. A user interface is presented that includes user interface controls associated with the identified elements of the unstructured text item. The user interface controls enable a user to control presentation of the unstructured text item in the identified elements in connection with applying the classification rule to the patient.

In general, in an aspect, an electronic medical record of a patient is maintained including unstructured text items and structured items relevant to a disease, condition, or procedure of the patient. The patient is automatically labeled for classification according to classification rules of a quality metric of service provided by healthcare provider to the patient. The automatic labeling includes automatically identifying factors in two or more of the unstructured text items and structured items, the factors corresponding to the classification rules of the quality metric.

These and other aspects, features, implementations, and advantages (1) can be expressed as methods, apparatus, systems, components, program products, business methods, means or steps for performing functions, and in other ways, and (b) will become apparent from the following description and from the claims.

DESCRIPTION

Figure 2:
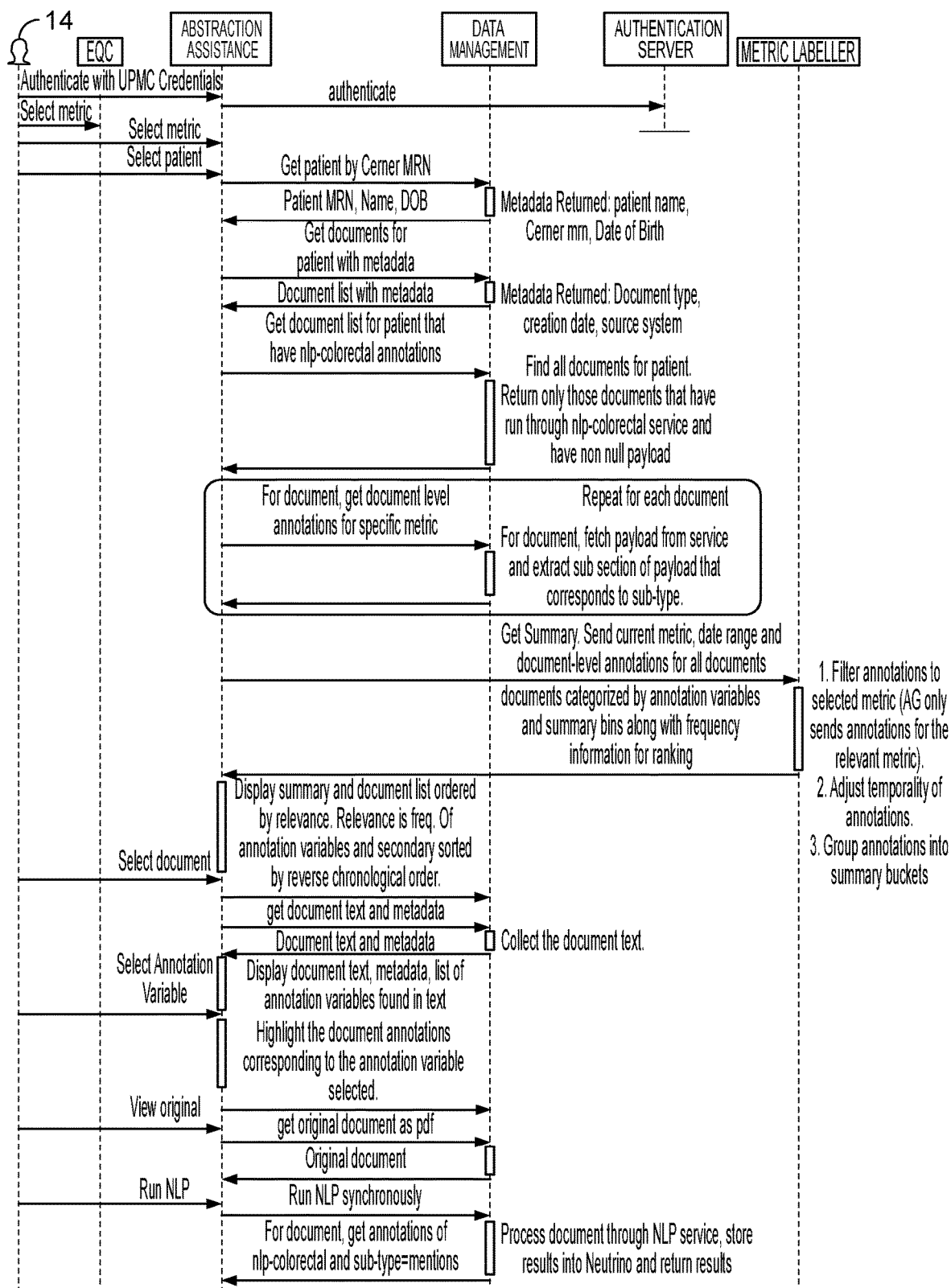

FIG. 1 is a block diagram.
FIG. 2 is a sequence chart.
FIGS. 3 through 12 are user interface pages.

INTRODUCTION

Here we describe a chart abstraction technology that, among other things, (1) preprocesses (identifies) items of a medical record, including unstructured natural language items, to identify elements of the items and generate annotations for the items relevant and useful to applying classification rules (or other types of rules) defined by quality metrics for patients served by providers with respect to particular diseases, conditions, or interventions; process different types of items in ways that are specific to the respective types; and recognize specific elements of items based in part on the types of items being processed (2) presents the items of the medical record and the identified elements and annotations of the items through a user interface for use by an abstractor to view, explore, contextualize, and abstract information from clinical documents, for use in applying classification or other rules within the context of quality metrics and workflows, (3) in some implementations, determines automatically and suggests to an abstractor through the user interface, whether a patient satisfies a classification or other rule of a quality metric, for example, whether the patient belongs in the numerator or the denominator, or in an exclusion category, and (4) in some cases, identifies and incorporates in the user interface presentation, elements derived automatically from structured items of the medical record (for example the date of a procedure).

This abstraction technology offers a variety of potential benefits. The technology can make chart abstraction easier, faster, less expensive, more comprehensive, more efficient, and more accurate. In addition, the abstraction technology can enhance population-wide quality improvement programs of providers, generate more revenue for providers participating in value-based care incentive models, yield a better image of the provider in the view of the public and payers, reduce service costs (e.g., treating sepsis more quickly can reduce patient length of stay), reduce readmissions, mortality, and infections, and improve patient experiences.

In some implementations, an additional value of the abstraction technology, because of its efficiency, is in applying quality metrics across a large population of patients (for example, every patient) belonging to the denominator of a fraction, rather than a smaller sampling that might otherwise result from limited resources. Complete measurement of quality metrics (by inclusion of all relevant patients) can improve acceptance of the results internally by a provider compared with quality metrics resulting from a smaller sample and can reduce resistance to programs aimed at improving quality metric performance. Complete measurement of quality metrics also can support targeted patient intervention, such as reminders to patients and providers designed to increase compliance with quality objectives. For example, colon cancer screening yields earlier diagnosis and fewer unnecessary colonoscopies. Early colon cancer diagnoses improve outcomes and reduce treatment costs.

In our discussion here, we often use examples, such as examples that relate to colon cancer, colonoscopies, and related diseases, conditions, and interventions. In addition to Measure #343 mentioned earlier, quality metrics related to such matters include OP-29, ASC-9: Appropriate Follow-up Interval for Normal Colonoscopy in Average Risk Patients; and OP-30, ASC-10: Colonoscopy Interval for Patients with a History of Adenomatous Polyps—Avoidance of Inappropriate Use. OP metrics (part of the Hospital OQR program) and ASC reports (part of the ASCQR program) are promulgated by Centers for Medicare and Medicaid Services (CMS) as part of its Ambulatory Surgical Center Quality Reporting (ASCQR) Program.

We sometimes use the quality metric of Adenoma Detection Rate (ADR) as an example for explaining the abstraction technology. ADR is considered a primary quality metric for screening colonoscopy and surveillance colonoscopy. ADR can be measured at the level of a provider, or an organization, group, or laboratory operating within a provider. Although ADR is used for purposes of illustration, a wide variety of other quality metrics and rules underlying them can be handled by the abstraction technology.

The Technology

Overview

As shown in FIG. 1, some implementations of the abstraction technology 10 include an abstraction assistance process 12 that, among other things, presents tools, controls, data, information, features, and functions through the Internet 16 and a browser-based user interface 18 to assist abstractors 14. The abstraction assistance process also can present its interface in other ways to abstractors, for example, through mobile apps or on computer workstations without using the Internet.

In some implementations, the user interface 18 presents a visualization 20 of a patient medical record 22 that facilitates work by the abstractors in applying classification rules 30 for quality metrics 32 for individual patients served by health care providers with respect to diseases, conditions, and interventions. The user interface enables abstractors to easily, quickly, and accurately view, navigate, analyze, and work with annotated unstructured items 24 (e.g., unstructured text items such as natural language clinical documents) and structured items 26 of the medical record. Through the user interface, the abstractor can, among other things, assign or confirm an automated assignment of the patient to one of two or more classifications 28 (such as the denominator and numerator of a fraction) according to metric classification rules 30 of quality metrics 32, based on the items of the medical record.

Medical Record System

To support the presentations that the abstraction assistance process provides to the abstractor in the user interface of the abstraction technology, a data management component 36 (which can be part of a comprehensive platform and technology framework 34 for health care management) can, among other things, ingest (from sources 38) and manage unstructured items 24 of the medical record (for example, prose notes of a physician), structured items 26 of the medical record, and definitions of quality metrics 32 including definitions and structured data representations of metric classification rules 30.

The data management component 36 ingests the items from a variety of sources 38 such as clinical operations, laboratories, test facilities, and physicians. The sources can be under the control of the provider or can be accessible to the provider from other parties subject to appropriate confidentiality controls. The sources can include commercially available electronic medical records systems such as Cerner 40 and EPIC 42 operated in facilities of the provider to accumulate and process, for example, items of medical records of patients.

Natural Language Processing

In some implementations of the technology, unstructured items (e.g., unstructured text items) ingested by the data management component and provided to the abstraction assistance process are first passed to a natural language processing service 40 (part of the platform and technology framework 34). In some cases, the abstraction assistance process coordinates the operation of the data management component and the natural language processing service and the use of the results of applying the natural language processing.

The natural language processing service 40 is an executable process that runs on a server and is accessible through a network from other servers and clients. The natural language processing service provides sophisticated natural language processing (NLP) of unstructured items to generate additional information (for example, annotations of the unstructured items) useful to the abstraction assistance process. Among the functions of the natural language processing service are to parse unstructured prose of unstructured items of medical records to identify words, phrases, and concepts relevant to the metric classification rules 30 underlying quality metrics. The natural language processing service performs these functions with respect to a variety of medical diseases, conditions, and interventions that may be the subject of abstraction work done by abstractors.

Typically, the parsing of a particular unstructured item of a medical record by the natural language processing service is based on quality metrics and classification rules associated with a particular disease, condition, or intervention. For example, the natural language processing could be applied to unstructured items that have been identified as relating to gastrointestinal matters (e.g., colonoscopy, screening, ADR).

For such processing, the natural language processing service could rely on a body of stored structured data 42 representing one or more specific quality metrics and classification rules related to colorectal matters. For example the natural language processing system could identify all gastrointestinal cancers based on a taxonomy of cancers derived from a controlled terminology that has been optimized for a specific quality metric or set of quality metrics. The body of stored structured data could include words, phrases, modifiers, relations, or concepts appearing in the defined quality metrics and their classification rules, synonyms for the words, phrases, or concepts, expressions of the rules to be applied in classifying patients, factors relevant to applying the rules (e.g., the age of the patient), structured information about exceptions, and other information. The taxonomies or other structured data representing quality metrics and classification rules can be produced by humans working in a user interface to review the prose versions of the quality metrics and the classification rules and to express corresponding taxonomies or other structured data. For example, the humans can identify conditions, diseases, and interventions, and characteristics stated in the rules for inclusion or exclusion in the numerator or the denominator. The taxonomies or other structured data can be expressed as graphs, for example. The result of the work can be stored in the natural language processing service for use there and in other places in the technology.

The stored structured data about the metrics and rules provides a body of information for the natural language processing service to use in identifying relevant words, phrases, modifiers, relations, and concepts in the unstructured items and then to create annotations of the unstructured items for use by processes applied later. In some cases, the natural language processing can include using metadata associated with the unstructured items and parsing the unstructured text item, recognizing words, phrases, and concepts, and creating corresponding annotations in part based on matching with the structured data representations (e.g., the graph) of the classification rules and quality metrics.

As a result of processing the unstructured items 24 provided from the data management component, the natural language processing service returns to the data management component annotations 46 for each of the ingested unstructured items. The data management component can store the annotations along with the unstructured items and use them to provide annotated versions of the unstructured items 48 to the abstraction assistance process 12, which can present them to the abstractor through the user interface. A natural language processing precision manager of the data management component can coordinate the return of the annotated items to the data management component and the storage of the annotated items by the data management component. The precision manager queues patients for processing by appropriate natural language processing services and stores results in the data management component for later retrieval and used by other parts of the technology.

The annotations of an unstructured item can include identifications of relevant elements (e.g., as reflected in the text) including words, phrases, concepts, conditions, diseases, interventions, diagnoses, recommendations, and temporal expressions required or useful for applications of rules, classification of patients, and computations of quality metrics by or with the assistance of the abstractor. These identified relevant elements in the text of an unstructured item are sometimes called "mentions". A mention can be, for example, the word "colonoscopy" in a physician's note.

The identified relevant elements can be presented (for example is highlighted portions of the text of presented items) through the user interface to the abstractor by the abstraction assistance process to support faster, easier, and more accurate processing by the abstractor. In the presentation through the user interface, the relevant elements (e.g., the mentions) can be highlighted, colored, flagged, or shown in unusual typefaces, font sizes, and other visual characteristics to make them especially noticeable to the abstractors. Relevant elements can be identified for the abstractor within original viewable versions of unstructured items, viewable versions of the texts of unstructured items, user interface controls, summaries of classifications, unstructured items, rules, or metrics, notes, and in other ways.

The data management component and the natural language processing service can communicate by software calls, if they both are running on the same processor, or through network communication if they are running on different processors. Generally, the data management component and the natural language processing service run as parts of the platform and technology framework 34 and for that purpose can run on a single server at one location, multiple servers that one location, or multiple servers at multiple locations interconnected by a network.

The information passed from the data management component to the natural language processing service to request natural language processing of an unstructured item, and the information returned by the natural language processing service to the data management component are sometimes referred to, respectively, as an incoming payload and an outgoing payload of the natural language processing service.

Examples of the incoming payload and the outgoing payload for the natural language processing service could take the following form:
Incoming Payload Requirements
    Interface
        Restful encrypted service (HTTPS)
        Support for a single POST API and synchronous/blocking payload NLP response.
        Support for a health endpoint to ensure that the service is working correctly.
    Natural language processing
        Support for one-to-one item-annotation generation to be associated with a specific item (e.g. an unstructured item). Provide configuration factors for service. Provide metadata that might be useful for natural language processing.
    Sample incoming payload:

```
{
"document_metadata":
{
"document_root":"EPIC.DOCUMENT.OID", //VALIDATION: Required Field "document_extension":"1234", //VALIDATION: Required Field
"date_of_service":"2010-12-17T12:49:00.000Z", //VALIDATION: UTC Time
"created_at":"2010-12-17T12:49:00.000Z", //VALIDATION: Required Field. Format: UTC Time "updated_at":"2010-12-17T12:49:00.000Z",
//VALIDATION: UTC Time
"document_type_root":"EPIC.DOCUMENT.OID",
//VALIDATION: Required
Field "document_type_extension":"RAD", //VALIDATION: Required Field "document_status":"preliminary/final/addendum",
//VALIDATION: Required Field
}
"compressed_text":"{base64(gzip(document_text))}" //VALIDATION:
Required Field. Format base64-gzipped UTF-8 text.
}
```

Outgoing Payload Requirements
    Provide metadata so this payload can be located again.
        Provide version info.
    Provide ability to bundle different annotation sets/groups in same payload
    Sample outgoing payload:

```
{
"service_id":"NobleService", "service_version":"1.0.0",
"software_version":"2.3.0", "ontology_version:"2.3.1",
"has_data":"true/false",
"ontology_uri":"http://ontologies.upmc.edu/domains/cmsColorectal
Metrics.owl",
"document_metadata": { "document_root": "EPIC.DOCUMENT.OID",
"document_extension": "123456",
"visit_extension": "123456", "document_type_root":
"EPIC.DOCUMENT.TYPE.OID", "document_type_extension":
"Consult Note", "date_of_service": "2017-01-01T20:47:45.000",
"created_at": "2017-01-01T20:47:45.000", "updated_at": "2017-01-01T20:47:45.000",
"facility_extension": "Grand Facility", "document_status" :
"final"
},
"OP29":{
"document_annotations":[//list of document level annotations],
"mention_annotations":[//list of mention level annotations]
}
"OP30":{
"document_annotations":[//list of document level annotations],
"mention_annotations":[//list of mention level annotations]
}
...
}
```

We sometimes refer to the outbound payload of the natural language processing service as "annotated items" or as "annotations". Annotations are mention level, item level, and patient level annotations. Patient level annotations (which are used in presenting the summary bar of the user interface) and item level annotations are performed by the metric labeler. Mention level annotations are performed by the natural language processing service.

Metric Labeling

Before presenting the items and annotations to the abstractors, the abstraction assistance process can cause additional processing of the items and annotations by sending them to a metric labeler 50. Based on the structured data 42 (e.g., the graphs) representing elements of classification rules 30 of quality metrics 32, the metric labeler processes a set of all of the items and annotations for a given patient to determine, among others things, whether together they suggest classification of the patient within the denominator of a quality metric or within the numerator of a quality metric or both. The metric labeler can perform this function using the structured data representing the classification rules, regardless of how information needed to apply the classification rules is phrased in the unstructured text.

As mentioned earlier, the structured data representing quality metrics 42 and corresponding classification rules can take the form of definitions generated using a description logic (e.g., a subset of first-order logic), such as can be expressed in the Ontology Web Language. In some implementations, the metric labeler uses an automatic theorem prover (or other techniques) to apply the definitions to the unstructured items (and in particular to the annotations) to classify then for inclusion in or exclusion from the numerator or the denominator and to classify the patient associated with the annotated items as possibly belonging to a specific classification (e.g., as belonging to a numerator or a denominator or a denominator exception).

For example, suppose a quality metric tests whether, for a specific group of patients (ages 50-75) having a disease A, a test B was performed within the last 3 years excluding patients having findings X, Y, or Z. Then the denominator would include patients (age 50-75) having disease A, but excluding those with findings X, Y, or Z, and the numerator would include patients in the denominator for whom test B was performed within the last 3 years. This test would be expressed (by a human coder) as structured data stored in the metric labeler (or outside the metric labeler and provided as input to the metric labeler) and would be applied by the metric labeler to the unstructured items and the related annotations to classify patients.

The metric labeler in a sense matches the annotations of the unstructured items with the formal structured data representing the classification rules and produces labels expressing classification states of the patient associated with the medical record containing the unstructured items. For this purpose, the metric labeler typically processes more than one unstructured item for the patient, for example, a set of unstructured items or an entire patient medical record.

The output of the metric labeler returned to the abstraction assistance process can include summaries of the determined classifications for the annotated items and for the patient under the relevant classification rules of the quality metric. The abstraction assistance process can use the labels of the patients and the summaries of the determined classifications generated by the metric labeler to present to abstractors suggestions, hints, reports, summaries, or confirmations of their classification work, among other things.

The work of the metric labeler is coordinated by the abstraction assistance process along with the coordination of the data management component and the natural language processing service.

In some implementations the incoming payload and the outgoing payload for the metric labeler could take the following form (where an item is an annotated unstructured item in the discussion above):

Input Requirements
    Restful encrypted service (HTTPS)
    Support for a single POST API and synchronous/blocking payload response.
    Support for a health endpoint to ensure that the service is working correctly.
    Provide metric, annotation year, and item level annotations for that metric for all items.

Sample Incoming Payload

```
{
"metric"="OP-29Metric",
"annotation_date"="2018-1-1T01:30Z",
"documents"=
[
{
"document_metadata": {
"document_extension"="12345", //VALIDATION: Required Field
"document_root": "EPIC.DOCUMENT.OID",
"document_type_root": "EPIC.DOCUMENT.TYPE.OID",
"document_type_extension": "Consult Note",
"date_of_service": "2017-01-01T20:47:45.000",
"facility_root:" "ROOT.OID",
"facility_extension:" "Grand Extension",
},
"document_annotations"=[//list of document level annotations for the selected metric]
},
{
"document_metadata": {
"document_id"="12345", //VALIDATION: Required Field
"document_type_root": "EPIC.DOCUMENT.TYPE.OID",
"document_type_extension": "Consult Note",
"date_of_service": "2017-01-01T20:47:45.000",
"created_at": "2017-01-01T20:47:45.000",
....
},
"document_annotations"=[//list of document level annotations for the selected metric]
}
...
]
}
```

Outgoing Payload Requirements
    Provide filtered set of item annotations grouped by group (bin) and item.

Sample Outgoing Payload

```
{
"bins"=
[
{
"name"="Numerator Inclusion",
"annotations"=
[
{
"name"="Follow_up_procedure_with_interval_gte_10_years_document",
"label"="Follow Up >10 Years",
"documents"=
[
{
"document_root"="EPIC.DOCUMENT.OID", //VALIDATION: Required Field
```

-continued

```
"document_extension"="5678", //VALIDATION: Required Field
"derived_from"=["Follow_up_procedure_with_interval_gte_10_years_
document_122"]
},
{
"document_root"="EPIC.DOCUMENT.OID", //VALIDATION: Required
Field
"document_extension"="1234", //VALIDATION: Required Field
"derived_from"=["Follow_up_procedure_with_interval_gte_10_years_
document_122"]
}
...
]
},
{
"name"="Colonoscopy_document",
"label"="Colonoscopy",
"documents"=
[
{
"document_root"="EPIC.DOCUMENT.OID", //VALIDATION: Required
Field
"document_extension"="5678", //VALIDATION: Required Field
"instance_count"="1"
},
{
"document_root"="EPIC.DOCUMENT.OID", //VALIDATION: Required
Field
"document_extension"="9876", //VALIDATION: Required Field
"instance_count"="2"
}
] //documents
}
] //annotations
},
{
"name"="Denominator Exclusion",
"annotations"=
[
{
"name"="Less_than_adequate_prep_document",
"label ="Inadeqate Prep.",
"documents"=
[
{
"document_root"="EPIC.DOCUMENT.OID", //VALIDATION: Required
Field
"document_extension"="5678", //VALIDATION: Required Field
"instance_count"="2"
},
{
"document_root"="EPIC.DOCUMENT.OID", //VALIDATION: Required
Field
"document_extension"="1234", //VALIDATION: Required Field
"instance_count"="1"
}
...
] //documents
},
...
] //annotations
}
]//bins
}
```

The metric labeler can be implemented as a process running on one or more servers, for example, the server or servers on which the platform and technology framework runs. In some implementations, the abstraction assistance process and the metric labeler can be processes running on the same server or can run on different servers and communicate with one another through a network.

Sequence Chart

As shown in FIG. 2, the sequence of the use of the abstraction technology by an abstractor can be illustrated by a diagram in which the entities involved in the process sequence are arranged in the diagram from left to right, and the activities involved in the sequence are arranged vertically from top to bottom. The entities include the abstractor 14, the EQC or another abstraction workflow management tool, the abstraction assistance process, the data management component, an authentication server, and the metric labeler. Each of the components comprises a process running on one or more servers or clients. Each of the components can run on its own server, or two or more the components can share server. The components can communicate with one another through networks.

As a first step of the sequence, the abstractor submits authentication credentials to the abstraction assistance process. The abstraction assistance process forwards the authentication credentials to the authentication server. Once the abstractor has been authenticated, he can begin to work in the user interface presented by the abstraction assistance process. As a first step, he can choose a quality metric to work on (for example, one of the colonoscopy quality metrics described above). Initially he can select the metric. In some implementations the following information can be loaded from a source system or the abstraction management workflow tool (e.g., EQC) The information can include patient name, medical record number, encounter identifier or FIN (financial identification number).

Next the abstractor selects the quality metric in the user interface of the abstraction assistance process. Then the abstractor selects a patient whose medical record will be analyzed with respect to the selected quality metric. To do this the abstractor can enter the patient's medical record number (MRN) and the FIN or other encounter identifier. Using the entered medical record number, the abstraction assistance process requests information about the patient from the data management component. The data management component fetches and returns metadata that includes a patient name, the medical record number, and the date of birth. The abstraction assistance process then makes a request to the data management component to provide unstructured items and structured items for that patient using the metadata related to that patient. The data management component fetches and returns metadata for a list of the unstructured items and structured items available for the patient. The metadata for each item on the list includes a item type (for example, a colonoscopy report, a pathology report, a nursing admission note, or an anesthesia pre-op note), a creation date, a financial identification number, and a identifier of the source of the item. The abstraction assistance process makes a request to the data management process for a list of items for the patient that have annotations from the natural language processing service. The data management component then locates items for the patient that have been processed by the natural language processing service and have non-null payloads (e.g., they have annotations).

Next the data management component and the abstraction assistance process cooperate to complete the following process for each of the items found. The abstraction assistance process requests, for each of the items, the annotations or the portion of the annotations that meets a certain specified sub-type of annotation or relate to a specific metric or both. For example, the subtype could be metric OP29 or metric OP30 and the request from the abstraction process could specify annotations for that metric at an item level or a mention level. The data management component fetches the payload for that item, extracts the portion of the payload that meets the specified sub-type (for example, mention level annotations with respect to a particular metric), and returns it to the abstraction assistance process.

Once the items and associated annotations (or portions of them) for that patient have been fetched and returned to the abstraction assistance process, the abstraction assistance process provides the items and associated annotations to the metric labeler and requests the metric labeler information to generate information about the patient for the current metric. The request to the metric labeler includes the current metric being worked on by the abstractor, g, and the annotations for all of the items or portions of items as prepared by the natural language processing service. The metric labeler analyzes the items or portions of items identified by the abstraction assistance process, filters the annotations to include only those that are relevant to the current metric (based on the annotations), and groups the annotations into summary groups, one for each classification defined by the classification rules. For example, there could be four groups for four respective classification rules: numerator inclusion, numerator exclusion, denominator inclusion, and denominator exception. The metric labeler then returns to the abstraction assistance process the annotations categorized by classification rules in the summary groups, and identifies which items contain which annotations and their frequency of appearance for use in ranking. The abstraction assistance process then displays to the abstractor through the user interface, a summary based on the summary groups and an item list ordered (ranked) by relevance with respect to the current metric. For this purpose, the relevance could be, for example, the frequency of appearance of annotation variables in the items. A secondary sorting of the items can in reverse chronological order, so that the top item appearing on the user interface of the abstractor is the most recent one with the highest frequency ranking.

Based on the presentation of the ranked order of items, the abstractor can select one of the items to review by invoking a corresponding control displayed in the user interface. The invoking of the control causes the abstraction assistance process to request the text of the item and metadata from the data management component. The data management component fetches the relevant text of the item and other metadata such as the physician's name and returns it to the abstraction assistance process. Then, for each item, the abstraction assistance process requests from the data management component annotations typically previously created by the natural language processing service. for which the sub-type of the annotations is the quality metric that the abstractor is working on. As noted earlier, sub-types enable the abstraction assistance process to request only specific annotations. A sub-type can be a combination of a quality metric and item level or mention level annotations. The data management component then, for each item, fetches the payload from the natural language process service and extracts the subsection of the payload that corresponds to the identified subtype (in this case the "mention"). The data management component returns the mention-level annotations to the abstraction assistance process which then displays them on the user interface presented to the abstractor. The abstractor can then view the text of the original item with the relevant words and phrases of the annotation highlighted or otherwise indicated. If the abstractor wishes to do so, the abstractor can invoke a control of the user interface to request the original version of the item, for example, as a PDF file. The original version is returned after being fetched by the data management component.

At any point in the process of using the user interface, the abstractor can, with respect to a particular item, request the running of the natural language processing service. Then the abstraction assistance process will cause the data management component to run the natural language processing service on that item. The data management component will store the results and return them as annotations from the natural language processing service for annotations that have the subtype, for example, mentions.

Using the sequence illustrated in FIG. 2, the abstractor can navigate through all of the relevant items for a patient and for a particular quality metric and view useful relevant annotations of the texts of the items that flag words, phrases, concepts, and other features of the items that are useful to the abstractor in understanding how to classify the patient. For each of the relevant items, the abstractor can view annotated versions of the unstructured item or actual items in, for example, PDF format. In this way, the abstractor can apply classification rules more easily, quickly, and effectively. When finished with classification of a patient, the abstractor can repeat the sequence for other patients with respect to the same quality metric. The abstractor can also switch to working on patients with respect to other quality metrics.

User Interface

Figure 3:
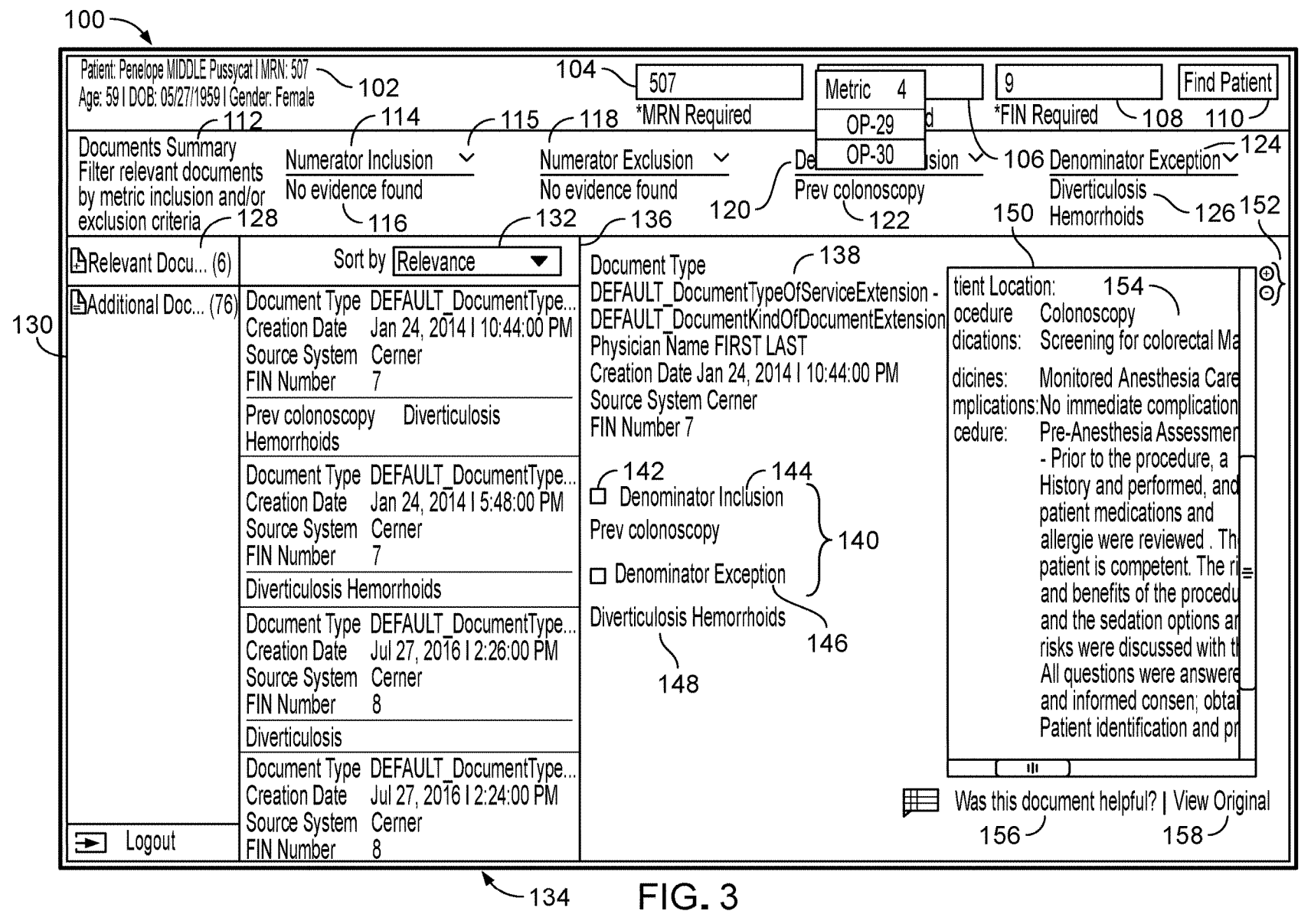

As shown in FIG. 3, the user interface 100 includes pages presented in a browser window. The abstractor can navigate through and use a variety of pages, controls, and viewers to work with unstructured items (and in some contemplated implementation structured items) of a medical record and to make and in some contemplated implementations to indicate decisions about classification rules for quality metrics, such as classification of a patient. In most of the pages of the user interface, an identification block 102 appears in the upper left corner that identifies the patient by name and medical record number and provides additional information about the patient, such as the age, date of birth, and gender. In the upper right-hand part of most pages, are boxes 104, 106, and 108 that enable the abstractor to focus her work. She can select a particular patient (by for example entering the patient medical record number in box 104), a particular quality metric (by using the drop-down list from box 106 (which lists only those quality metrics that are available for the abstractor to work on), and a financial identification number (identified in box 108). When a patient medical record number has been inserted in the box 104, the abstractor can click on the button 110 to cause the abstraction assistance process to query the data management component to attempt to identify the particular patient in its stored records.

Below the identification information shown in the top of each page is an items summary bar 112 that enables an abstractor to view a current summary of classifications (summary groups) of the patient's medical record items and of the patient (a patient level summary) across all unstructured data items available for the patient, based on classification rule factors. In the illustrated example, the items summary bar has four panels 114, 118, 120, and 124 for displaying and controlling information about inclusion of the patient in the numerator, exclusion of the patient from the numerator, inclusion of the patient from the denominator, and exceptions to the denominator. The items summary bar enables easy navigation by the abstractor of all of the items for the patient that are available through the user interface. For this purpose, the items are grouped among the four classifications based on the presence of evidence (mentions or labels, for example) for each of the items. Under each of the headings for each of the four classifications, the user interface presents information about classification factors for which there is evidence in documents related to the patient.

In the presentation mode shown in FIG. 3, each of the four classification sections displays current information with respect to each of the factors for which evidence existed. For example, no evidence was found 116 in any of the processed items for this patient for numerator inclusion or for numerator exclusion. However, evidence was found in one or more of the items for the factor that the patient had a previous colonoscopy 122 and therefore could be properly included in the denominator. Evidence also was found in one or more of the items for the factors diverticulosis and hemorrhoids 126 (which are bases for denominator exception). A down arrow 115 next to each of the panel headings enables the abstractor to open the panel for viewing additional controls with respect to the factors for which there was evidence (see FIG. 9). The additional controls enable the abstractor to filter the available processed items to include only the ones that contain the evidence for the factors checked by the abstractor. This enables the abstractor to narrow and re-narrow as needed the set of processed items that the abstractor is currently working with for this patient.

The classification of the patient as illustrated in the items summary bar can be based on all of the applicable structured items and unstructured items of the patient's medical record and on the elements in those items (evidence) supporting factors associated with the quality metric. For example, in the state of classification of the patient as of a stage in the abstractor's work shown in FIG. 3, the basis for inclusion of the patient in the denominator was the existence of a previous colonoscopy as determined by the presence of relevant words, clauses, or concepts in one or more of the unstructured items. In addition, the patient met the factors for an exception under the part of the classification rule referring to diverticulosis and hemorrhoids.

Below the items summary bar on many of the pages of the user interface, on the left side of the page is a navigation panel 134 that displays information about structured items and unstructured items associated with the identified patient. The panel 134 provides tabs 128 and 130 on the left side which enable the user to view presentations of relevant items or additional items for the patient. Relevant items can include unstructured items which have been automatically identified by the natural language processing service or the metric labeler as including elements indicating that the items may be relevant to classification work with respect to the identified quality metric. Additional items can include structured items and unstructured items that are part of the patient's medical record. The additional items may or may not be of interest to the abstractor; but either way they have not been identified as especially relevant by the natural language processing service, the metric labeler, or the abstraction assistance process.

On the right side of the panel 134 is a subpanel that includes a vertical arrangement of "cards" each providing general descriptive information about a corresponding unstructured item or structured item. For example, the card 136 contains information identifying the item type, the creation date, the system that was the source of the item, and the financial identification number. Underneath the identifying information on the card is a section that identifies factors representing grounds for classifications under classification rules based on elements identified in the unstructured item. These factors can be displayed using different colors corresponding to colors used for display in the four panels of the items summary bar. For example, one color is used (according to the item summarized in card 136) to indicate inclusion of the patient in the denominator based on a previous colonoscopy. In another color, the card also indicates that the item included elements reflecting diverticulosis and hemorrhoids in the patient indicating denominator exceptions (which also appear in the same color in the items summary bar above).

The cards in the panel 134 can be sorted in various ways. In the situation shown in FIG. 3, they have been sorted according to relevance 132, with the item considered by the abstraction assistance process to be the most relevant (based on the work of the natural language processing service and the metric labeler) at the top.

The abstractor can select an item by clicking on the corresponding card in panel 134. On the right side of many of the pages of the user interface, as shown in FIG. 3, a panel 150 presents a text version 154 of a particular item, in this case the item at the top of the set of cards in panel 134. Also associated with panel 150 are controls 152, 156, and 158. The controls 152 enable the abstractor to enlarge or reduce the scale of the display shown in the panel. The control 156 can be invoked by the abstractor to indicate the quality of the work done by the metric labeler and the natural language processing service in determining that the item had a high relevance. The control 158 can be invoked to display to the user an original (for example, PDF format) version of the item in case that would be useful to the abstractor.

In the center of many of the pages of the user interface, as shown in FIG. 3, is a portion 138 that enables the abstractor to view, in the text version 154 of a particular item, highlights or other indicators of words or phrases that comprise mentions of relevant factors used by the abstraction assistance technology in making classification decisions based on the classification rules for the identified quality metric. At the top of that central portion of the page, information about the item being viewed in panel 150 is shown, including the item type, the name of the physician, the creation date of the item, the system that was the source of the item, and the financial identification number. Below that information, the list of factors related to the quality metric that were identified in the item by the natural language processing service are displayed. The factors are organized by classification rule into numerator inclusion, numerator exclusion, denominator inclusion, or denominator exclusion. Of the four, checkboxes are displayed only for those classification rules for which factors were identified in the displayed item by the natural language processing service. In this example, the displayed factors are for denominator inclusion and denominator exception, because only those factors were identified in elements of the displayed item. The user interface shows that the patient had a previous colonoscopy. If the abstractor wishes to see the elements in the displayed item that supported the determination that the patient had had a previous colonoscopy and therefore might be included in the denominator, the abstractor checks the checkbox 142. Similarly, the checkbox labeled denominator exception as the words "diverticulosis" and "hemorrhoids" shown beneath it. By checking the checkbox 146, the abstractor is presented with highlighting or other indications of the elements in the displayed item that supported a determination that the patient met the denominator exception classification rule.

Therefore, the central section 138 of many pages of the user interface enables the abstractor to see the determinations of the metric labeler about classification of the patient under the relevant classification rules at the item level (related to the displayed item) and also enables the abstractor to select or deselect highlighting of the relevant evidence in the displayed item that supported the determination.

In some implementations (not illustrated in FIG. 3), controls can be provided for the abstractor not only to view and navigate the work and conclusions of the natural language processing service and the metric labeler, but also to participate in the process of classification directly in the user interface. In other words, the abstractor can commit to classification determinations within the user interface rather than being required to switch to another user interface (for example, EQC, in order to express those classification determinations.

As can be seen in FIG. 3, the same factors for inclusion and exception are reproduced in the items summary bar above FIG. 4 illustrates that if the abstractor clicks on one of the factors 168 associated with a classification rule for a quality metric, the basis on which of the natural language processing service and the metric labeler determined the existence of those factors is highlighted 170 in the text of the displayed item and also highlighted 171 on card 169.

Figure 5:
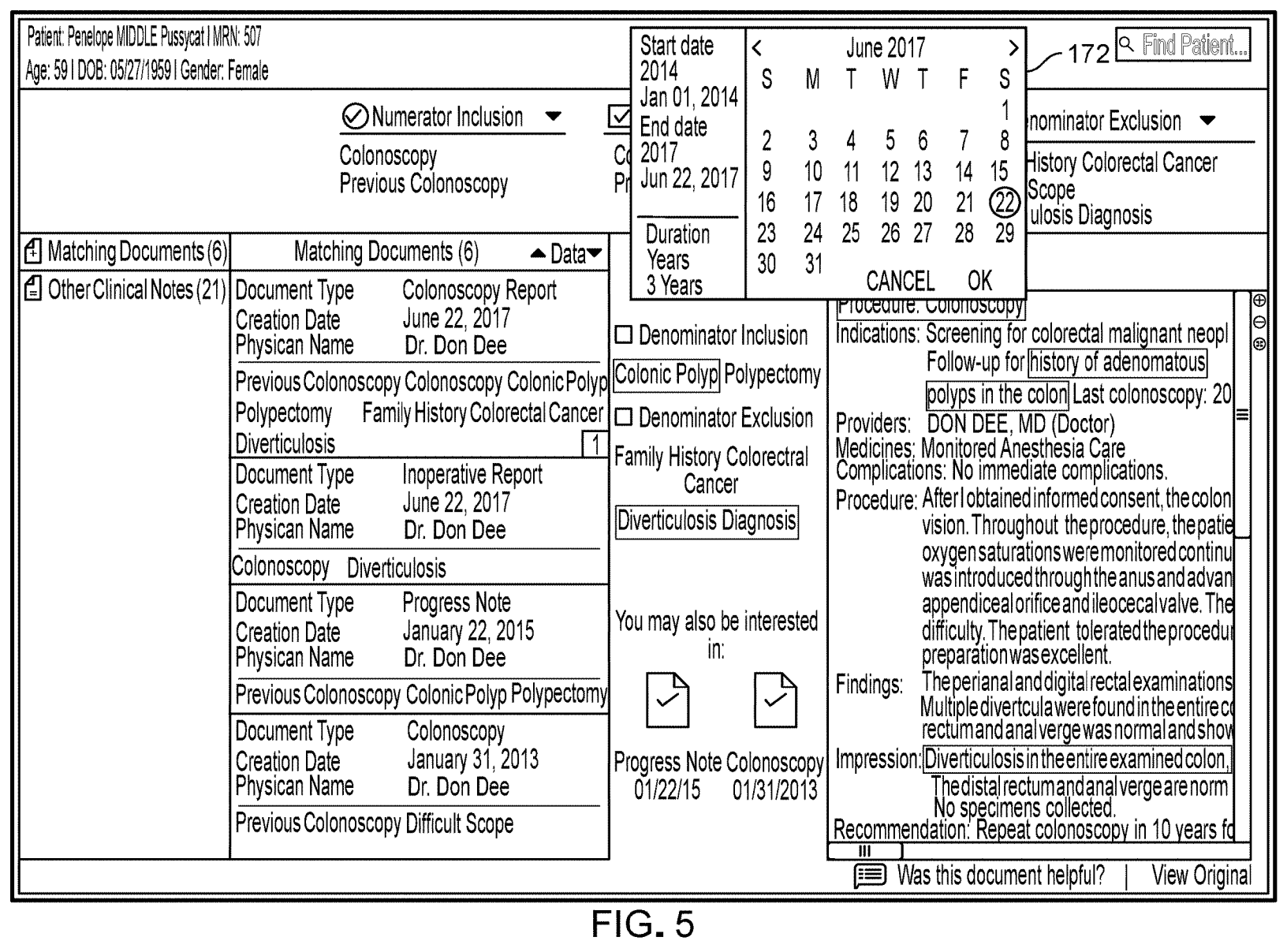

As shown in FIG. 5, in some implementations, an additional respect in which the abstractor can filter the structured items and unstructured items that will be presented to her is by a range of dates of the items using a calendar dialog box 172. As shown in FIG. 6, the result of that filtering is displayed in box 174 and governs which items will be displayed in panel 134.

Figure 7:
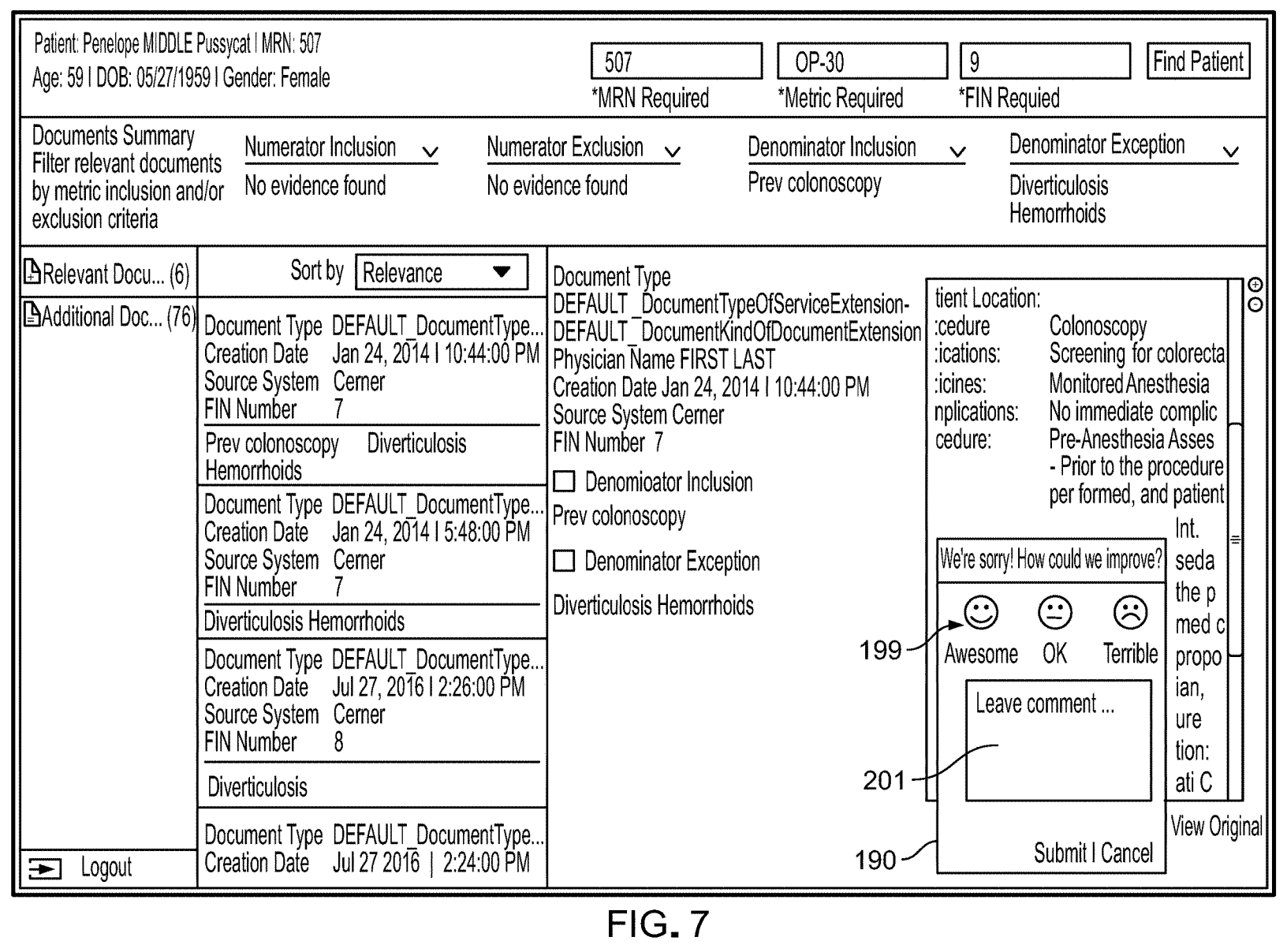

As shown in FIG. 7, when an abstractor invokes the control 156 ("Was this item helpful?") The dialog box 190 appears enabling the abstractor to choose one of three icons 199 representing three different choices of the feedback to be given. A text box 201 provides space for the abstractor to type prose comments.

Figure 8:

As shown in FIG. 8, the cards in panel 134 can be sorted by the abstractor invoking one of the options in a list box 192 including relevance, date, financial identification number, or document type.

Figure 9:
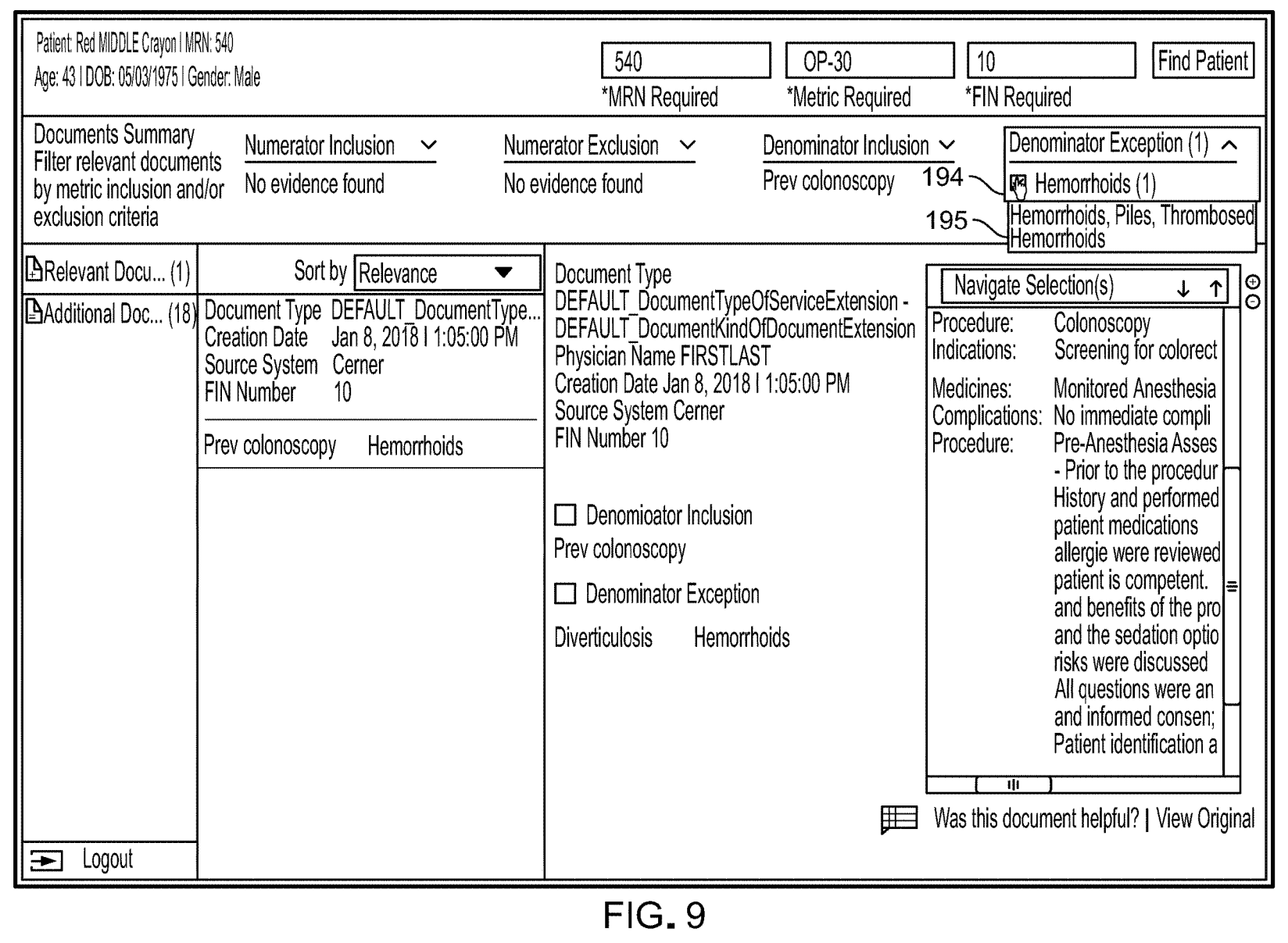

As shown in FIG. 9, when an abstractor invokes the down arrow in one of the items of the items summary bar she can view the classification factors and can check a checkbox for a factor associated with the inclusion, exclusion, or exception rule. In this case the mouse pointer is hovering over the factor "hemorrhoids" causing a sub box 195 to open identifying the factor (in this case, "hemorrhoids, piles, thrombosed hemorrhoid"). Checking sub boxes in the list causes a filtering of the items list in panel 169 to show only items that exhibit the factors associated with the checked sub boxes. This enables the abstractor define what she wants quickly across the whole set of items available through the user interface.

Figure 10:
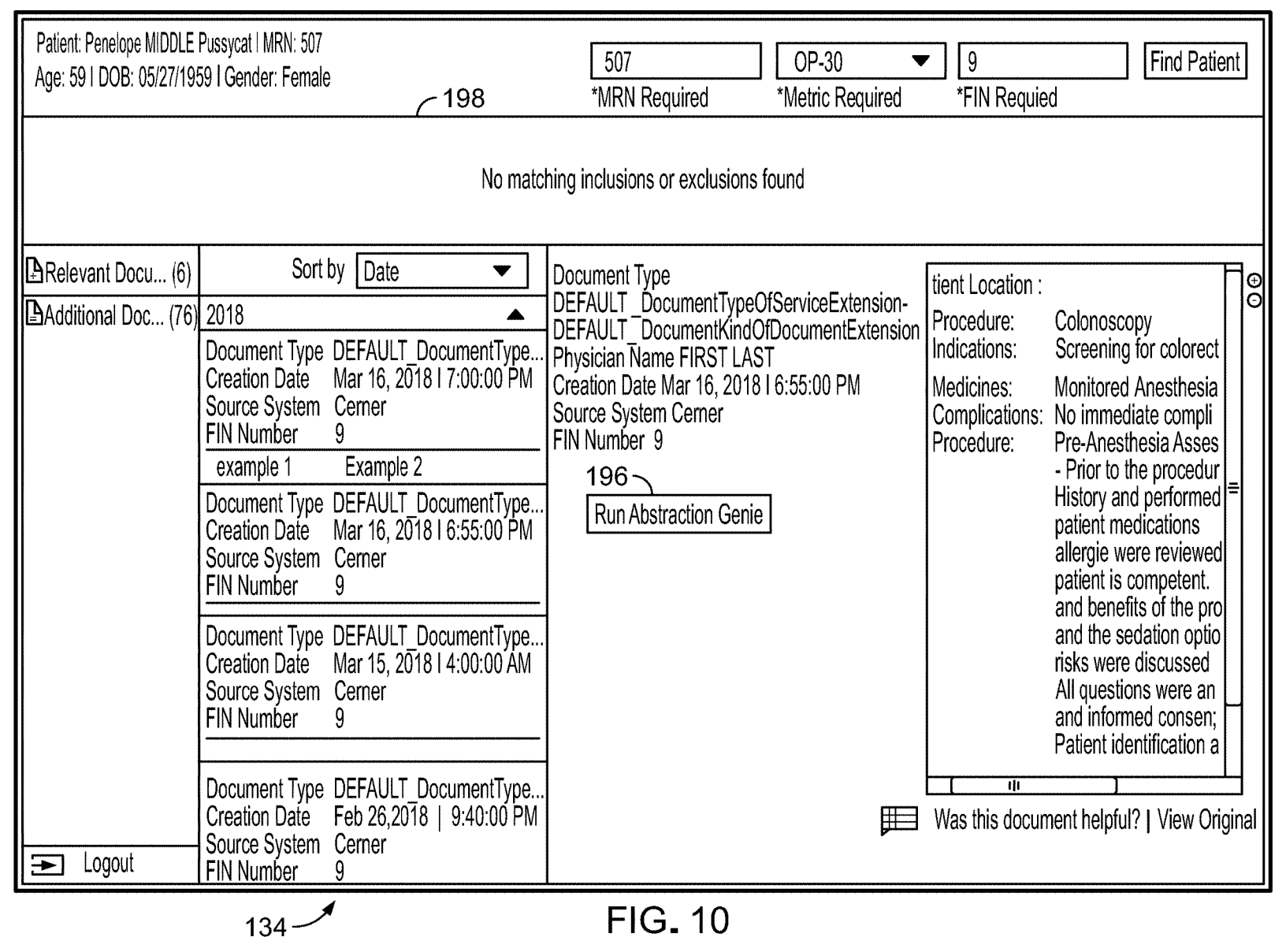

As shown in FIG. 10, with respect to any of the items whose cards appear in the panel 134 and are invoked by the abstractor, the abstractor can invoke a control 196 to run or rerun the natural language processing service and the metric labeler with respect to that item. The result is to cause the abstraction assistance process to have the item analyzed to determine whether it includes words, phrases, or concepts that are evidence for inclusion, exception, or exclusion of the patient with respect to classification rules of the quality metric. If the abstraction assistance process is able to determine that there is no evidence in the item for such an inclusion, exclusion, or exception, the banner 198 confirming that fact to the abstractor can be presented.

Figure 11:
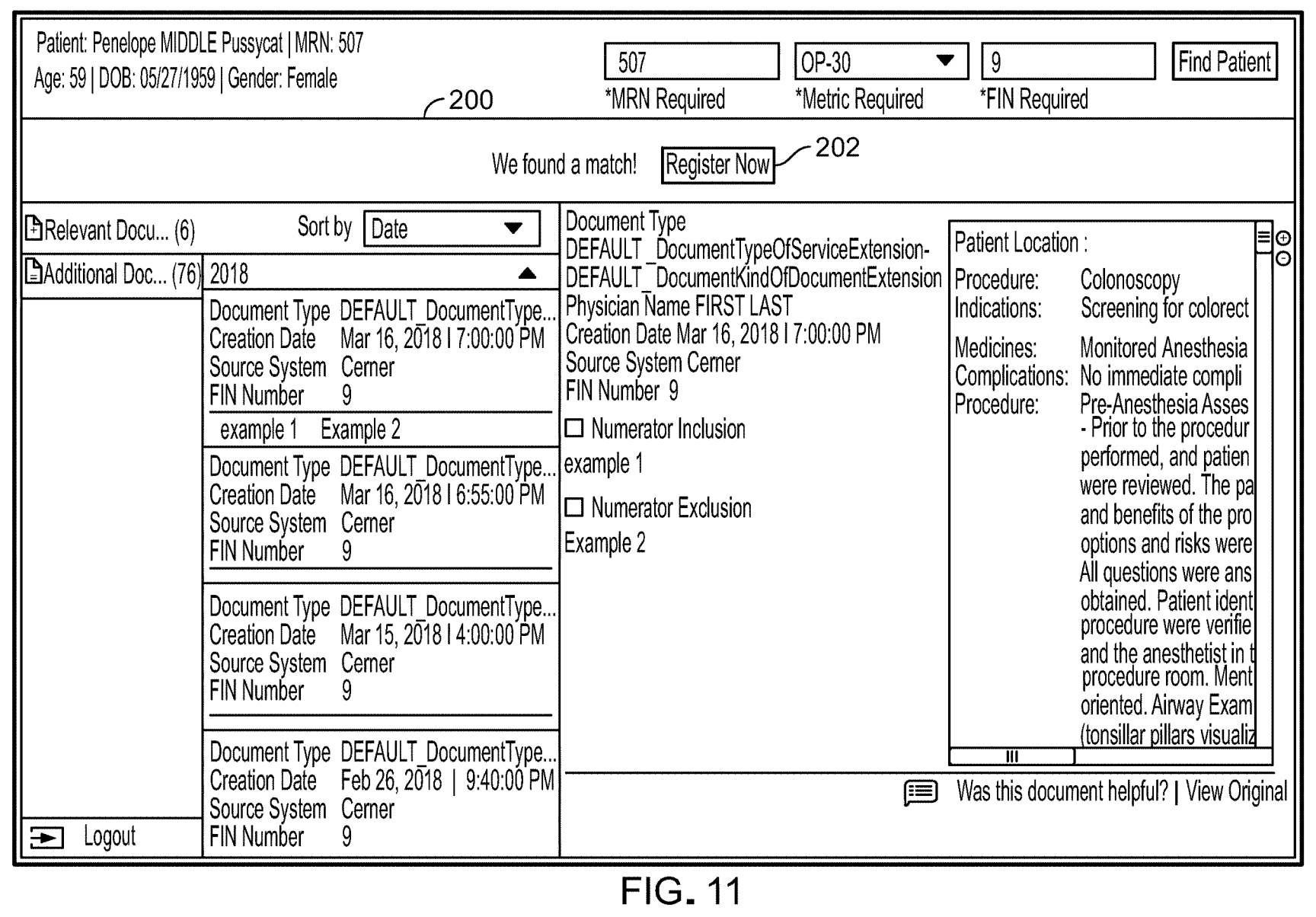
Figure 12:
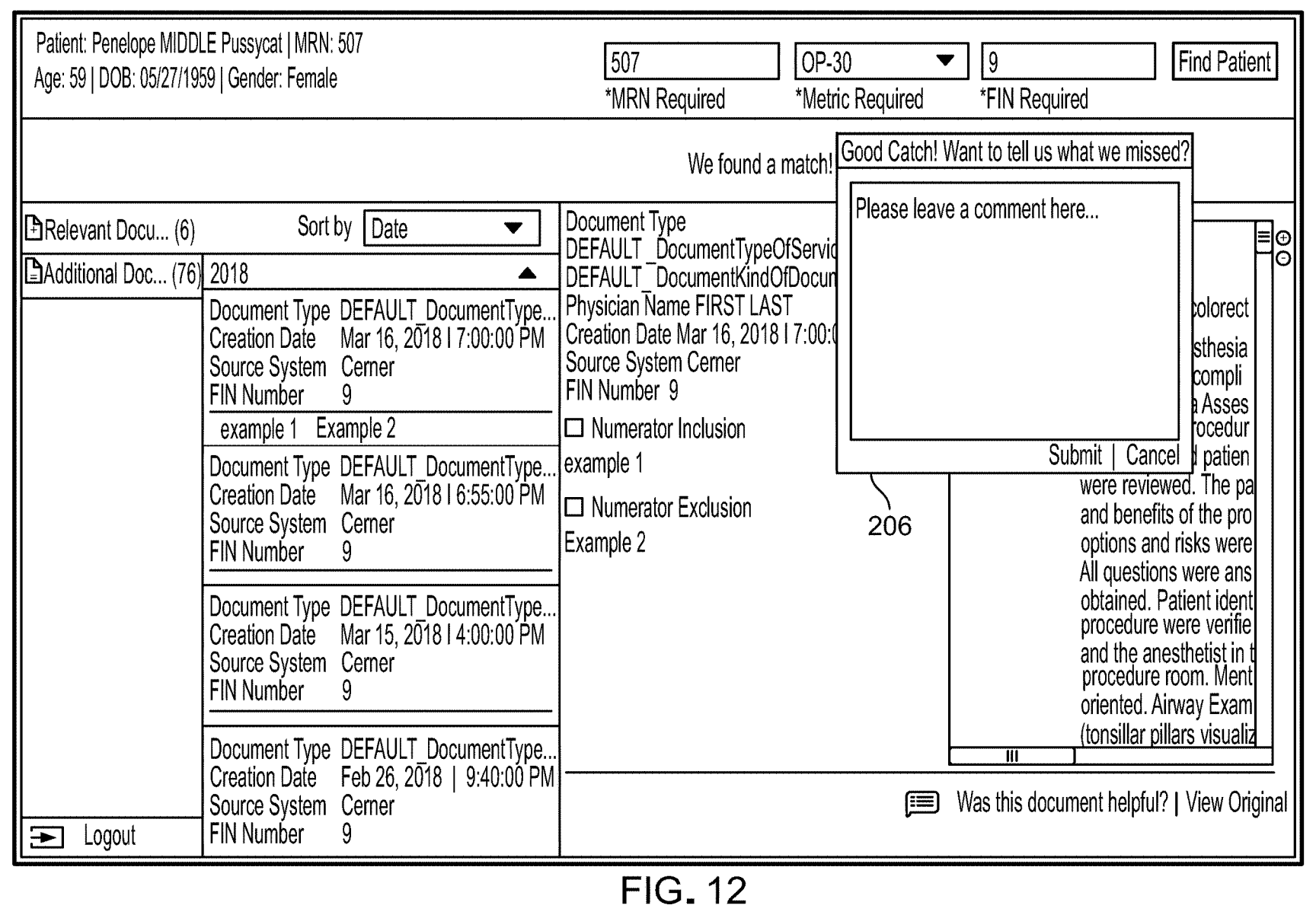

As shown in FIG. 11, on the other hand, if evidence has been found for such an inclusion, exclusion, or exception, the banner 200 is presented indicating this result. A button 202 is also presented to the abstractor to report feedback to the development team that a match was found. Invoking button 202 causes the dialog box 206 of FIG. 12 to appear enabling the abstractor to write and submit a text comment explaining why the determination of a match was incorrect.

In the user interface, items in the medical record 22 (FIG. 1) that are determined to contain relatively more relevant information for applying the classification rules are given priority in the medical record visualization 20 over items that contain lessons relevant information. For example, the priority can be reflected in the positions of the components in a list presented to the abstractor. This prioritization enables the abstractor to work quickly to verify the information, classify the patient according to the classification rules, and move to processing the medical record of another patient.

The features and functions of the user interface and the abstraction assistance process together enable an abstractor to work more quickly, easily, and effectively. She can navigate the available items for all patients of a provider with respect to all possible quality metrics and all possible facilities of the provider. She can then select a particular facility, quality metric, and an individual patient (and a succession of patients) whose disease, condition, or intervention is relevant to that quality metric. If useful, she can then indicate a date range of interest for items to be considered. Once the patient has been selected, the abstractor is presented with an ordered list of cards or other brief synopses of items of the medical record of the patient that have been pre-determined (by the natural language processing service and the metric labeler) to be relevant to factors of the classification rules for the selected quality metric as expressed in the structured data representing the classification rules. She can reorder the cards based on relevance, date, or other sorting criteria to make navigation easier. Any card can be invoked to cause the corresponding item to be displayed and relevant elements of the item to be highlighted. She is also presented with factors of the classification rules that are supported by the elements highlighted in the displayed item. These factors can be pre-identified by the natural language processing service and the metric labeler.

In some contemplated implementations, the abstractor cannot only review and consider the correctness of the results produced by the natural language processing service and the metric labeler, but also can confirm or undo the classification or perform the classification directly. In such implementations, as work progresses a summary of the classification state of the patient would be continually presented so that the abstractor could gauge progress in the abstraction work and the correctness of the determined classifications as of any point in the work.

By enabling cooperation of a human abstractor and automated natural language processing, metric labeling, and abstraction assistance, the abstraction assistance technology empowers the abstractor to work more quickly, accurately, carefully, confidently, and efficiently in the abstraction process for each patient, each metric, and each classification rule. She can perform more abstraction tasks in less time reducing cost or enhancing the scope, breadth, depth, and comprehensiveness of the quality metrics, facilities, and patient populations that can be processed.

The abstraction assistance technology also can include features for measuring the performance of the technology and of abstractors who use it. One feature could measure the abstraction speed per patient categorized by abstractor and by metric. An average speed for abstracting a patient by metric and by abstractor could then be determined and used to gauge speed improvements and identify issues. Another feature could identify items of medical records that were unmatched for each abstractor and each metric. Unmatched items can be, for example, those determined not to be relevant to classification rules or quality metrics by the natural language processing service and the metric labeler) but which the abstractor either used in classification or flagged as mishandled by the automated processes. The goal would be a very low number of items per patient implying that abstractors found the information they needed in the items found to be relevant by the natural language processing service and the metric labeler. For similar purposes, the abstraction assistance technology can aggregate and analyze the number and character of feedback entries provided by abstractors across all abstractors and metrics and in other ways.

In various implementations of the abstraction technology, the participation, control, authority, and performance by the abstractor, and the relationship between the abstraction technology and other applications, such as abstraction assistance workflow management tools can differ significantly.

In some cases, the abstraction decisions about classification of patients using classification rules is completely controlled by the abstractor and expressed through features of the separate abstraction assistance workflow management tools. In such cases, the abstraction technology assists the abstractor by enabling the abstractor to navigate the items of each patient's medical record with respect to various quality metrics, to filter and sort the items, to review evidence of factors of the classification rules determined by the metric labeler and the natural language processing service, and to view the evidence in the context of displayed versions of the texts of the items, among other features. But the actual expression of the classification decisions is made by the abstractor through the abstraction assistance workflow management tools.

In some instances, the functions provided by assistance workflow management tools can be incorporated in and integrated with the functions of the abstraction technology described earlier. In such instances, the abstractor can operate in the same manner described above but can do so entirely within a single user interface.

In some examples, the abstractor's role in the functions performed by her in the user interface are not limited to her making and expressing the classification decisions herself, but can also include the abstraction technology determining (for example, in the ways described earlier), displaying, and completely automatically determining the results of the process of classification. In such examples, the role of the abstractor can be to review the items with respect to the patient while observing the automatically determined classifications and then either simply approving them or correcting them as needed.

In some implementations, even more authority can be given to the automatic processes that determine the classifications so that the abstractor is no longer involved in reviewing or correcting some of them. For example, the abstraction technology could display and request approval by the abstractor only of classification determinations for which the abstraction technology had more than a threshold level of uncertainty. As a simple example, in some situations, the abstraction technology can be relied on to automatically classify patients as belonging to the denominator of a fraction based on interpretation of the text of clinical notes or other unstructured items or structured items.

To support the development of implementations involving a range of involvement by abstractors relative to automated activities by the abstraction technology, a variety of abstraction performance measurements and comparisons between the work of human abstractors and the work of automated processes of the abstraction technology can be devised and applied. In some implementations, separate user interfaces can be provided for developers and managers of abstractors to review, analyze, and otherwise work with the definition, application, and results of such measurements and comparisons.

For example, the annotation technology can measure performance of annotators in a variety of ways. Timed trials can be applied to measure how long it takes for an abstractor to classify a patient. The comparative reliability of different abstractors in their classifications of patients can be measured. The performance of fully automated classifications done by the annotation technology can be compared with the performance of manual classifications by human abstractors and with the performance of hybrid systems involving partially automated classification assisted by human abstractors. Performance of manual abstractors, automated abstraction, and hybrid abstraction can be compared to a gold standard for abstraction performance. In some cases, the annotation technology can also provide tools, tips and functions to cause human abstractors to perform their tasks in standardized ways based on defined standard practices and to measure and report variations of actual performance against the standards.

In some implementations of the user interface, a separate tab can be made available only to developers and managers of abstractors. Among the information provided on the user interface pages available in such a tab could be data on the time required by a each abstractor to complete the abstraction of each patient. The abstraction technology could provide additional information by calculating statistical summaries of the timing data, such as the average time per patient and the standard deviation by abstractor, by metric, and by reporting program. In such calculations, the abstraction technology can normalize the number of items considered to account for differences in the numbers of items in respective medical records.

With respect to measuring the consistency of the performance by two or more abstractors, the abstraction technology can calculate an interrater agreement between abstractors when they have abstracted the same patient using standard measures of agreement such as Cohen's Kappa, Fleiss's coefficient, or Krippendorff's alpha depending on the relevant data. The abstraction technology can present this data through the user interface to the abstraction managers or other developers as a table of correlations so that they can identify abstractors who are abstracting differently than other abstractors.

In some implementations, similar calculations can be performed by the abstraction technology to determine calculate agreement between individual annotators and a gold standard defined by the abstraction managers or other developers, for example. The abstraction technology will present this data through the user interface tab as a table of correlations that abstraction managers or other developers can use to identify abstractors who are abstracting differently than the gold standard.

In some implementations, the user interface presented to the abstraction managers or other developers can provide tools to alter definitions of classification metrics, for example, available to abstractors when they invoke controls in there tabs of the user interface so that the abstractors have a consistent, immediately available, and contextualized definition of how given classification metric should apply to a specific patient. This feature will be used to help abstractors to standardize against the accepted definition.

In some implementations, the user interface presented to abstraction managers or other developers can provide data and tools to enable assessing whether automated performance of the abstraction technology compares favorably enough to abstraction performance of humans to permit full automation of the abstraction task. The user interface can also provide a control enabling an abstraction manager or developer to cause automated classification to be done at once for all patients of a large data set. For this purpose, the abstraction technology can present through the user interface to the abstraction manager or other developer a table of correlations. The displayed correlations can be between performance of individual abstractors of a set of abstractors or between performance of individual abstractors and performance of a gold standard, or between performance of individual abstractors or a set of abstractors and performance of automated operation of the abstraction platform. The abstraction manager or developer then can determine whether there is a significant difference in accuracy (defined by precision and recall) of the automated abstraction technology compared to a human standard. The manager or developer can have the option to partially or completely automate the computation of a given metric depending on that determination. When this automated process has been started by the manager or developer, the abstraction technology will start automatic population of the metric questions (see below). The manager or developer will be able to select the eligible population using dates, and ICD (international classification of disease) and CPT (current procedural terminology) data as suggested below.

In some implementations of the abstraction technology, information would be accumulated and saved about the classification judgments made by human abstractors in addition to automated classification determinations made by the abstraction technology. In essence this would eliminate the need for a separate abstraction workflow management tool such as EQC.

For this purpose, the abstraction technology can provide through the user interface sets of questions that correlate to the structured data expressing the classification rules so that answers to the questions with respect to a patient would determine correctly if the patient is in a denominator population or denominator exclusion, and if the patient belongs in the numerator or not. The user interface could enable the abstractor to indicate whether she agreed with the basis for the abstraction technology placing a particular patient in a summary group or not. The abstractors indication within the saved and made available through the tab accessible by the abstraction manager to illustrate instances of disagreement between the human abstractors and the automated operation of the abstraction technology.

In some implementations, the abstraction technology can provide a "human-in-the-loop" active learning approach that enables the abstraction technology to adapt the knowledge and logic of its executable processes as it detects differences between classifications made by human abstractors and automated classifications, and presents them to the abstractor.

For example, the abstraction technology can adapt to decisions and assessments made by human abstractors that differ from automated classification decisions made by the abstraction technology. For this purpose, the abstraction technology can track differences between the classification decisions made by human abstractors and automated classification decisions. When a specific annotation factor (e.g., a combination of an anchor such as colonoscopy and associated modifiers (e.g. present, certain, experienced by the patient, temporality=<10 years ago) falls below a specific threshold of agreement of the automated classification with classification by human abstractors, the abstraction technology can use the abstractor data as training data, specifically by determining surrounding context of words and features and using ontology learning to identify new lexical cues for the associated annotation factor.

In some implementations, the abstraction technology can be closely or loosely integrated with one or more electronic medical record systems that are operated internally or externally to a given provider. The abstraction technology can then directly use information in the electronic medical record system for its functions and activities and can return information to the electronic medical record system for example to notify a provider about inadequate performance in providing healthcare to patients. For this purpose, the abstraction technology can be integrated with the electronic medical record system into "directions". The abstraction technology can accept ICD and CPT codes needed or useful in determining an eligible population (e.g. all patients who have billing codes for screening or surveillance colonoscopies or flexible sigmoidoscopies and therefore fall within the denominator of a metric). In the abstraction technology can transmit quality metrics (determine manually, automatically, or in a hybrid system) to the electronic medical record system for corresponding patients. Such information can then be reported directly to caregivers for the specific patients to assist in improving the delivery of healthcare to the specific patients.

Other implementations are also within the scope of the following claims.

The invention claimed is:

1. A method comprising by computer, processing text of medical records of each patient of a group of patients who received health care services for a particular disease, condition, or intervention from a particular hospital or other health care providing arrangement, the particular hospital or other health care providing arrangement being subject to a defined metric of quality of its performance as a hospital or other health-care providing arrangement in providing the health care services to the group of patients for the particular disease, condition, or intervention, the defined metric of quality being established by a party independent of the hospitals or other health care providing arrangements, the defined metric of quality also being applied uniformly to other hospitals or other health care providing arrangements for comparison of the relative performances of hospitals or other health care providing arrangements, the defined metric applying, statistically across the group of patients, to the provision of the health care services by the particular hospital or other health care providing arrangement for the particular disease, condition, or intervention, the defined metric including numbers and computational components applied to the numbers, one or more of the numbers being occurrences of inclusion of one or more of the patients as having received health care services provided by the particular hospital or other health care providing arrangement for the particular disease, or intervention that satisfy a classification standard, and at least one of the numbers being occurrences of exclusion of one or more of the patients as not having received health care services provided by the particular hospital or other health care providing arrangement for the particular disease, condition, or intervention that satisfy a classification standard the computer being configured to find automatically, in the processing of the text, words or phrases based on whether they indicate that the health care services were provided by the particular hospital or other health care providing arrangement to each of the patients for the particular disease, condition, or intervention in accordance with a defined process associated with the defined metric, the text of the medical records being in a form of unstructured natural language text that is otherwise incapable of evaluation by the defined metric until after it is standardized into a structured form through natural language processing;

the computer being configured to receive from a user identifications of which individual patients satisfy inclusion criteria and which individual patients satisfy exclusion criteria for inclusion in or exclusion from the numbers of the defined metric, by computer, evaluating the defined metric of quality of its performance as a hospital or other health care providing arrangement, the evaluation of the defined metric comprising (a) receiving from the user the identifications of inclusion in or exclusion from the numbers, (b) calculating each of the numbers based on the received identifications of inclusion or exclusion, and (c) applying the computational components to the calculated numbers to generate a value of the defined metric across all of the patients of the group of patients statistically, and by computer, reporting the generated value of the defined metric to another party as an indicator of the quality of the performance of the particular hospital or other health care providing arrangement in providing the health care services to the group of patients for the particular disease, condition, or intervention and as an indicator of the performance of the particular hospital or other health care providing arrangement relative to the performance of one or more other hospitals or other health care providing arrangements.

2. The method of claim 1 in which the processing of the text comprises specifying annotations or other metadata for the text, the metadata comprising factors of the inclusion criteria or the exclusion criteria.

3. The method of claim 2 in which the metadata for the text comprises one or more types of metadata.

4. The method of claim 3 comprising maintaining structured data representing the inclusion criteria or the exclusion criteria and in which the specifying of metadata for the text is based on the structured data representing the inclusion criteria or the exclusion criteria.

5. The method of claim 1 in which the processing of the text is also to identify concepts, modifiers, or relationships associated with the inclusion criteria or the exclusion criteria.

6. The method of claim 1 comprising, through a user interface, presenting a user interface control for specifying a range of dates, and in which items of the text presented to each of the users are within the range of dates.

7. The method of claim 1 in which the text comprises clinical notes or reports of a practitioner.

8. The method of claim 1 in which the defined metric is applied to the group of patients to generate a fraction.

9. The method of claim 8 in which the defined metric comprises a denominator representing a fraction of the group of patients having specified characteristics.

10. The method of claim 9 in which the defined metric comprises a numerator representing a fraction of the group of patients who belong to the denominator and for whom the disease, condition, or intervention for which the health care services were provided by the particular hospital or other health care-providing arrangement have specified factors.

11. The method of claim 10 in which the denominator of the fraction comprises a number of patients satisfying first inclusion criteria or exclusion criteria-for inclusion or exclusion of patients and the numerator of the fraction comprises a number of patients satisfying a second inclusion criteria or exclusion criteria for inclusion or exclusion of patients.

12. The method of claim 1 comprising presenting by the computer, through a user interface, text identified based on relevance status to the inclusion criteria or the exclusion criteria.

13. The method of claim 12 comprising presenting by the computer text in orders based on dates or relevances.

14. The method of claim 1 comprising presenting by the computer of a summary of classification statuses of each of the patients with respect to the inclusion criteria or the exclusion criteria.

15. The method of claim 1 comprising by computer, receiving defined structured classification rule data representing the defined metric, and by computer, processing the text to find words or phrases of the text that correspond to words or phrases appearing in the inclusion criteria or the exclusion criteria-and using the defined structured classification rule data representing the inclusion criteria or the exclusion criteria to generate indications of conformity of the text with the inclusion criteria or the exclusion criteria.

16. The method of claim 15 in which the text comprises human-generated prose.

17. The method of claim 16 in which the human-generated prose comprises words, phrases, or concepts.

18. The method of claim 15 in which the defined metric comprises fractions and the inclusion criteria or the exclusion criteria-define criteria for inclusion in the numerators or the denominators of the fractions.

19. The method of claim 15 comprising by computer, populating user interface tools with the text, the identified elements of the text, and the indications of conformity of the text with the inclusion criteria or the exclusion criteria.

20. A method comprising by computer, processing text of medical records of each patient of a group of patients who received health care services for a particular disease, condition, or intervention from a particular hospital or other health care providing arrangement, the particular hospital or other health care providing arrangement being subject to a defined metric of quality of its performance as a hospital or other health-care providing arrangement in providing the health care services to the group of patients for the particular disease, condition, or intervention, the defined metric of quality being established by a party independent of the hospitals or other health care providing arrangements, the defined metric of quality also being applied uniformly to other hospitals or other health care providing arrangements for comparison of the relative performances of hospitals or other health care providing arrangements, the defined metric applying, statistically across the group of patients, to the provision of the health care services by the particular hospital or other health care providing arrangement for the particular disease, condition, or intervention, the defined metric including numbers and computational components applied to the numbers, one or more of the numbers being occurrences of inclusion of one or more of the patients as having received health care services provided by the particular hospital or other health care providing arrangement for the particular disease, or intervention that satisfy a classification standard, and at least one of the numbers being occurrences of exclusion of one or more of the patients as not having received health care services provided by the particular hospital or other health care providing arrangement for the particular disease, condition, or intervention that satisfy a classification standard the computer being configured to find automatically, in the processing of the text, words or phrases based on whether they indicate that the health care services were provided by the particular hospital or other health care providing arrangement to each of the patients for the particular disease, condition, or intervention in accordance with a defined process associated with the defined metric, the text of the medical records being in a form of unstructured natural language text that is otherwise incapable of evaluation by the defined metric until after it is standardized into a structured form through natural language processing;

classify automatically each of the patients as included or excluded in or from at least one of the numbers of the defined metric, present to a user through a user interface, information about the patient and the health care services provided by the hospital or other health care providing arrangement , enable a user to confirm through the user interface whether the automatic classification of inclusion or exclusion is correct, if the user confirms the correctness of the automatic classification, automatically evaluate the defined metric, report the generated value of the defined metric to another party as an indicator of the quality of the performance of the particular hospital or other-health care-providing arrangement in providing the health care services to the group of patients.

* * * * *